(12) United States Patent
Stauss et al.

(10) Patent No.: US 12,227,756 B2
(45) Date of Patent: Feb. 18, 2025

(54) ENGINEERED REGULATORY T CELL

(71) Applicant: UCL Business Ltd, London (GB)

(72) Inventors: Hans Stauss, London (GB); Graham P. Wright, London (GB); Jenny L. McGovern, London (GB)

(73) Assignee: UCL Business Ltd, London (GB)

( * ) Notice: Subject to any disclaimer, the term of this patent is extended or adjusted under 35 U.S.C. 154(b) by 950 days.

(21) Appl. No.: 17/048,587

(22) PCT Filed: Apr. 17, 2019

(86) PCT No.: PCT/GB2019/051097
§ 371 (c)(1),
(2) Date: Oct. 17, 2020

(87) PCT Pub. No.: WO2019/202322
PCT Pub. Date: Oct. 24, 2019

(65) Prior Publication Data
US 2021/0145884 A1    May 20, 2021

(30) Foreign Application Priority Data

Apr. 18, 2018 (GB) .................................. 1806330
Apr. 18, 2018 (GB) .................................. 1806331

(51) Int. Cl.
| | | |
|---|---|---|
| *A61K 35/17* | (2015.01) | |
| *A61K 39/00* | (2006.01) | |
| *C07K 14/725* | (2006.01) | |
| *C07K 14/74* | (2006.01) | |
| *C12N 5/0783* | (2010.01) | |
| *C12N 15/87* | (2006.01) | |
| *A61K 35/12* | (2015.01) | |
| *A61K 38/00* | (2006.01) | |

(52) U.S. Cl.
CPC .............. *C12N 15/87* (2013.01); *A61K 35/17* (2013.01); *A61K 39/4611* (2023.05); *A61K 39/4621* (2023.05); *A61K 39/4632* (2023.05); *A61K 39/46433* (2023.05); *C07K 14/7051* (2013.01); *C07K 14/70539* (2013.01); *C12N 5/0637* (2013.01); *A61K 2035/122* (2013.01); *A61K 38/00* (2013.01); *C12N 2510/00* (2013.01)

(58) Field of Classification Search
CPC ....................................................... A61K 35/17
See application file for complete search history.

(56) References Cited

U.S. PATENT DOCUMENTS 7,131,958 B2    11/2006    Deverre
7,147,626 B2    12/2006    Goodman et al.
2014/0004133 A1   1/2014    Bykovskaia et al.

FOREIGN PATENT DOCUMENTS

| WO | WO 2009/050283 A1 | 4/2009 | |
|---|---|---|---|
| WO | WO 2014/145970 A1 | 9/2014 | |
| WO | WO 2014/183056 A1 | 11/2014 | |
| WO | WO 2016133779 A1 | 8/2016 | |
| WO | WO 2017/062035 A1 | 4/2017 | |
| WO | WO-2021079120 A1 * | 4/2021 | ......... C07K 14/4713 |

OTHER PUBLICATIONS

Mailer (Front. Immunol. Mar. 13, 2018; 9: 530; pp. 1-11).*
Fransson et al. (J. Neuroinflammation. 2012; 9: 112; pp. 1-12).*
Adair et al. (Front. Immunol. Sep. 21, 2017; 8: 1117; pp. 1-10).*
Meinl et al. (Clin. Exp. Immunol. Jun. 2002; 128 (3): 395-7).*
Nguyen et al. (Biochem. Soc. Trans. Nov. 1, 2021; 49 (5): 2319-31).*
Kwon et al. (Proc. Natl. Acad. Sci. USA. Jan. 9, 2018; 115 (2): E253-E262).*
Bell et al. (J. Biol. Chem. Sep. 9, 1994; 269 (36): 22758-63).*
Georgiev et al. (J. Clin. Immunol. Oct. 2019; 39 (7): 623-40; author manuscript; pp. 1-31).*
Marriuza et al. (J. Biol. Chem. Jan. 2, 20204; 295 (4): 914-925).*
Kim et al. (J. Autoimmun. Aug. 2018; 92: 77-86; electronically published May 30, 2018; author manuscript; pp. 1-25).*
Walker et al. (J. Clin. Invest. Nov. 1, 2003; 112 (9): 1437-43).*
Yagi et al. (Int. Immunol. Nov. 2004; 16 (11):1 643-56).*
Chen et al. (Immunology. Sep. 2018; 155 (1): 123-136).*
Li et al. (Cell. Mol. Immunol. Sep. 2015; 12 (5): 558-65).*
Jardine et al. (Front. Immunol. 2013; 4: 495; pp. 1-9).*
Hall et al. (Int. Immunol. Apr. 1991; 3 (4): 359-68).*
Chatenoud et al. (Methods Mol. Biol. 2011; 677: 3-13).*
Akamatsu et al. (Sci. Immunol. Oct. 25, 2019; 4 (40): eaaw2707; pp. 1-16).*
Muraro et al. (J. Clin. Invest. Jul. 15, 1997; 100 (2): 339-49).*
Mcgovern et al. (J. Autoimmun. Oct. 2022; 132: 102888; pp. 1-7).*
Rudensky (Immunol. Rev. May 2011; 241 (1): 260-8; pp. 1-12).*
Peng et al. (J. Autoimmun. Jun. 2007; 28 (4): 188-200).*
Victoria Riddell, "Generating ag-specific human regulatory T-cells by TCR gene transfer for the treatment of rheumatoid arthritis", (Thesis), 2019, Ediburgh Napier Univeristy.
Altschul S F et al., Basic Local Alignment Search Tool, J. Mol. Biol., 1990, p. 403-410 (FASTA package).
Ausubel et al., Short Protocols in Molecular Biology, 1999, 4th edition, chapter 18 (BLAST package).
Ausubel et al., Short Protocols in Molecular Biology, 1999, 4th edition, pp. 7-58 to 7-60.
Coffin et al "Retroviruses" 1997 Cold Spring Harbour Laboratory Press Eds: JM Coffin, SM Hughes, HE Varmus pp. 758-763.

(Continued)

*Primary Examiner* — Stephen L Rawlings
(74) *Attorney, Agent, or Firm* — Grimes & Yvon LLP

(57) ABSTRACT

The present invention relates to an engineered regulatory T cell (Treg) comprising a T cell receptor (TCR) which is capable of specifically binding to a myelin basic protein (MBP) peptide or variant or fragment thereof when the peptide is presented by a major histocompatibility complex (MHC) molecule. The present invention further relates to methods for providing an engineered Treg and to methods and uses of said engineered Treg and vectors and kits of vectors encoding said Treg.

11 Claims, 18 Drawing Sheets

Specification includes a Sequence Listing.

(56) References Cited

OTHER PUBLICATIONS

Cohen C J et al., Enhanced Antitumor Activity of T Cells Engineered to Express T-Cell Receptors with a Second Disulfide Bond, Cancer Res. Apr. 15, 2007; 67(8): 3898-3903.
Devereux J et al., A comprehensive set of sequence analysis programs for the VAX, Nucl. Acid Res., 12:387-395 (1984).
Donnelly M et al., The 'cleavage' activities of foot-and-mouth disease virus 2A site . . . occurring '2A-like' sequences, Journal of General Virology, 2001, vol. 82, pp. 1027-1041.
Folch G & Lefranc M P, The human T cell receptor beta variable (TRBV) genes, Exp Clin Immunogenet, 2000, vol. 17, pp. 42-54.
Hodges E et al., Diagnostic role of tests for T cell receptor (TCR) genes, J Clin Pathol, 2003, vol. 56(1), pp. 1-11.
Huh J et al., Limited repertoire of HLA-DRB1*0401-restricted MBP111-129-specific T cells . . . and their pathogenic potential, Journal of Neuroimmunology, 2004, vol. 151, pp. 94-102.
Adair, Patrick et al., Human Tregs Made Antigen Specific by Gene Modification: The Power to Treat . . . Precision; Frontiers in Immunology. vol. 8:1117 (2017); doi: 10.3389/fimmu.2.
Bank, Ute et al., Inhibition of alanyl-aminopeptidase on CD4+ CD25+ regulatory . . . in mice; International Journal of Molecular Medicine. vol. 20, pp. 483-492 (2007).
Dawson, N. et al., Engineered Tolerance: Tailoring Development . . . Specificity of Regulatory T Cells; Frontiers in Immunology. vol. 8:1460 (2017); doi: 10.3389/fimmu.2017.01460.
Fransson, M. et al., CAR/FoxP3-engineered T regulatory cells target the CNS . . . intranasal delivery; Journal of Neuroinflammation. vol. 4, No. 9112, pp. 1-12 (2012).
Huang, J. et al., Histone/protein deacetylase 11 targeting promotes Foxp3+ Treg function; Scientific Reports. vol. 7, No. 8626 (2017).
Kim, Y.C. et al., Engineered myelin basic protein (MBP)-specific human T regulatory . . . in vivo; Journal of Immunology. vol. 198, No. 1 (2017).
Kim, Y.C. et al., Engineered MBP-specific human Tregs ameliorate MOG-induced EAE through . . . T cells; Journal of Immunology. vol. 92, pp. 77-86 (2018).
Lu, Y. et al., Rapamycin Regulates iTreg Function . . . Pathways; Journal of Immunology Research. vol. 2014, pp. 1-8 (2017).
Luth, S. et al., Ectopic expression of neural autoantigen in mouse liver . . . Tregs; Journal of Clinical Investigation. vol. 118, No. 10, pp. 3403-3410 (2008).
Mekala, D. et al., IL-10-dependent infectious tolerance . . . T lymphocytes; PNAS. vol. 102, No. 33, pp. 11817-11822 (2005).
Muraro, P. et al., Immunodominance of a Low-Affinity . . . T Cell Receptor Repertoire; Journal of Clinical Investigation. vol 100, No. 2, pp. 339-349 (1997).
Peng, J. et al., The effect of foxp3-overexpressing . . . lung cancer cells; Molecular Medicine Reports. vol 17, pp. 5860-5868 (2018).
Quandt, J. et al., Unique Clinical and Pathological . . . Transgenic Mice; Journal of Experimental Medicine; vol. 200, No. 2, pp. 223-234 (2004).
Riddell, V., Generating Ag-specific Human Regulatory . . . Arthritis; Thesis for Edinburgh Napier University; pp. 1-82 (2018).
Singh, K. et al., Concomitant analysis of Helios and Neuropilin-1 . . . naive mice; Scientific Reports. vol. 75, No. 7767 (2015).
Stephens, L. et al., Curing CNS autoimmune disease with myelin-reactive Foxp3+ Treg; Thesis for University of Edinburgh. pp. 1-28 (2017).
Tuohy et al., Preemptive targeting of the epitope spreading cascade . . . during EAE; Clarivate Analytics. (2017).
Zhao, G. et al., growth Ar-Specific 6 Enhances the Suppressive Function of . . . Axl Receptor; Mediators of Inflammation. vol. 2017, pp. 1-13 (2017).
Yiyuan Yin, et al., "Structure of a TCR with high affinity for sef-antigen reveals basis for escape from negative selection", EMBO J., 2011, vol. 30, pp. 1137-1148.
MMDB, 3O6F: Crystal Structure of a Numan Autominnune Tcr Ms2-3c8 bound to Mhc class liSelf-ligand Mbp/hla-dr4, Sep. 2011; Retrieved Feb. 13, 2023; URL: https://www.ncbi.nlm.nih . . . .
GenPept Accession No. 3O6 F_C, Chain C, and T-cell Receptor Alpha Chain Cregion, uploaded Sep. 7, 2011; Retrieved Feb. 13, 2023; URL: https://www.ncbi.nlm.nih.gov/protein . . . .
GenPept Accession No. 3O6 F_D, Chain D, and T-cell Receptor Beta-1 Chain C Region, uploaded Sep. 7, 2011. Retrieved Feb. 13, 2023; URL: https://www.ncbi.nlm.nih.gov/protein . . . .
Dun Zhou, et al., "High throughput analysis of TCR-β rearrangement and gene expression in single T cells", Lab. Invest., 2006, vol. 86, pp. 314-321.
Divya J. Mekala & Terrence L. Geiger, "Immunotherapy of autoimmune encephalomyelitis with redirected CD4+ CD25+ T lymphocytes", Blood, 2005, vol. 105, pp. 2090-2092.
Alla L. Zozulya & Heinz Wiendl, "The role of regulatory T cells in multiple sclerosis", Nat. Clin. Pract. Neurol., 2008, vol. 4, pp. 384-398.
Koop, B.F. et al. The human T-cell receptor TCRAC/TCRDC (CdαCδ) region: Organization, sequence and evolution of 97.6 kb of DNA, Genomics, 1994, 19, pp. 478-493.
Kuball J et al., Facilitating matched pairing and expression of TCR chains introduced into human T cells, Blood. Mar. 15, 2007; 109(6), pp. 2331-2338.
Lefranc M-P et al., IMGT unique numbering for immunoglobulin and T cell receptor . . . V-like domains, Developmental & Comparative Immunology, 2003, vol. 27, issue 1, pp. 55-77.
Lewis P et al., Human immunodeficiency virus infection of cells arrested in the cell cycle, EMBO J., 1992, vol. 11, No. 8, pp. 3053-3058.
Papworth, C, Bauer J C, Braman J and Wright D A, QuikChange site-directed mutagenesis, Strategies, 1996, vol. 9(3), pp. 3-4.
Scaviner D & Lefranc M-P, The Human T Cell Receptor AlphaVariable (TRAV) Genes, Exp Clin Immunogenet, 2000, vol. 17, pp. 83-96.
Wright G P et al., Adoptive therapy with redirected primary regulatory T cells results . . . suppression of arthritis, Proc Natl Acad Sci, Nov. 10, 2009, vol. 106, No. 45, pp. 19078-19083.
Zhou D et al., High throughput analysis of TCR-βrearrangement and gene expression in single T cells, Laboratory Investigation, 2006, vol. 86, pp. 314-321.

* cited by examiner

SEQ ID NO. 18 - Alpha Chain: V-region, MS2.3C8-alpha-variable(Va26-2) nucleotide Sequence:

CCCGGACCGATGAAGCTCGTGACCAGCATCACCGTGCTGCTGAGCCTGGGCATTATGGGCGACGCCAAGACC
ACCCAGCCCAACAGCATGGAAAGCAACGAAGAGGAACCCGTGCATCTGCCCTGCAACCACAGCACCATCAGC
GGCACCGACTACATCCACTGGTACAGACAGCTGCCCAGCCAGGGCCCCGAGTATGTGATCCACGGCCTGACC
AGCAACGTGAACAACCGGATGGCCTCCCTGGCCATTGCCGAGGACAGAAAGAGCAGCACCCTGATCCTGCAC
CGGGCCACCCTGAGAGATGCCGCCGTGTACTACTGCACCGTGTACGGCGGAGCCACCAACAAGCTGATCTTC
GGCACCGGCACACTGCTGGCCGTGCAGCCCAATATCCAGAACCCCGAC

FIG. 13

SEQ ID NO. 19 - MS2.3C8-alpha-variable(Va26-2) amino acid sequence:

DAKTTQPNSMESNEEEPVHLPCNHSTISGTDYIHWYRQLPSQGPEYVIHGLTSNVNNRMASLAIAEDRKSSTLILHR
ATLRDAAVYYCTVYGGATNKLIFGTGTLLAVQPNIQNPD

FIG. 14

SEQ ID NO. 13 – Amino acid Sequence: human V-region and murine C-region

CDR1, CDR2, CDR3, Murine constant region

DAKTTQPNSMESNEEEPVHLPCNHSTISGTDYIHWYRQLPSQGPEYVIHGLTSNVNNRMASLAIAEDRKSSTLILHR
ATLRDAAVYYCTVYGGATNKLIFGTGTLLAVQPNIQNPDPAVYQLKDPRSQDSTLCLFTDFDSQINVPKTMESGTFI
TDKCVLDMKAMDSKSNGAIAWSNQTSFTCQDIFKETNATYPSSDVPCDATLTEKSFETDMNLNFQNLSVMGLRIL
LLKVAGFNLLMTLRLWSSGSG

FIG. 15

SEQ ID NO. 20 - MS2.3C8 Beta Chain: human V-region
ATGCTTCTCCTTCTGCTGCTGCTGGGACCCGGCATCTCACTGCTGCTGCCTGGATCTCTGGCCGGCTCTGGACT
GGGAGCTGTGGTGTCTCAGCACCCCTCTTGGGTCATCGCCAAGAGCGGCACCAGCGTGAAGATCGAGTGCAG
AAGCCTGGACTTCCAGGCCACCACCATGTTTTGGTACAGGCAGTTCCCCAAGCAGAGCCTGATGCTGATGGCC
ACCTCCAACGAGGGCAGCAAGGCCACATATGAGCAGGGCGTGGAAAAGGACAAGTTCCTGATCAACCACGCC
AGCCTGACCCTGTCCACCCTGACAGTGACAAGCGCCCACCCCGAGGACTCCAGCTTCTACATCTGTAGCGCCA
GAGGCGGCAGCTACAACAGCCCTCTGCACTTTGGCAACGGCACCCGGCTGACCGTGACC

FIG. 16

SEQ ID NO. 21 - MS2.3C8 Beta chain: human V-region amino acid sequence:

GAVVSQHPSWVIAKSGTSVKIECRSLDFQATTMFWYRQFPKQSSCSWPPPTRAPRPPTSRASRRTSSSSTTPPSPS
PPSPSPPPTPRTPPSTSAPPAAAPTTPPSTSATAP

FIG. 17

SEQ ID NO. 14 – Amino acid sequence: human V-region and murine C-region

CDR1, CDR2, CDR3, Murine constant region

GAVVSQHPSWVIAKSGTSVKIECRSLDFQATTMFWYRQFPKQSLMLMATSNEGSKATYEQGVEKDKFLINHASLT
LSTLTVTSAHPEDSSFYICSARGGSYNSPLHFGNGTRLTVTEDLRNVTPPKVSLFEPSKAEIANKQKATLVCLARGFFP
DHVELSWWVNGKEVHSGVCTDPQAYKESNYSYCLSSRLRVSATFWHNPRNHFRCQVQFHGLSEEDKWPEGSPK
PVTQNISAEAWGRADCGITSASYHQGVLSATILYEILLGKATLYAVLVSGLVLMAMVKKKNS

FIG. 18

SEQ ID NO. 22 - MS2.3C8-alpha-variable amino acid sequence excluding CDR sequences

DAKTTQPNSMESNEEEPVHLPCNHSIHWYRQLPSQGPEYVIHVNNRMASLAIAEDRKSSTLILHRATLRDAAVYYC

FIG. 19

SEQ ID NO. 23 - MS2.3C8-beta-variable amino acid sequence excluding CDR sequences GAVVSQHPSWVIAKSGTSVKIECRSLMFWYRQFPKQSLMLMATTYEQGVEKDKFLINHASLTLSTLTVTSAHPEDS
SFYIC

FIG. 20

SEQ ID NO. 24 -Nucleic acid sequence encoding FOXP3

GAATTCGTCGACATGCCCAACCCCAGACCCGGCAAGCCTTCTGCCCCTTCTCTGGCCCTGGGACCATCTCCTGG
CGCCTCCCCATCTTGGAGAGCCGCCCCTAAAGCCAGCGATCTGCTGGGAGCTAGAGGCCCTGGCGGCACATTC
CAGGGCAGAGATCTGAGAGGCGGAGCCCACGCCTCTAGCAGCAGCCTGAATCCCATGCCCCCTAGCCAGCTG
CAGCTGCCTACACTGCCTCTCGTGATGGTGGCCCCTAGCGGAGCTAGACTGGGCCCTCTGCCTCATCTGCAGG
CTCTGCTGCAGGACCGGCCCCACTTTATGCACCAGCTGAGCACCGTGGACGCCCACGCCAGAACACCTGTGCT
GCAGGTGCACCCCCTGGAAAGCCCTGCCATGATCAGCCTGACCCCTCCAACCACAGCCACCGGCGTGTTCAGC
CTGAAGGCCAGACCTGGACTGCCCCCTGGCATCAATGTGGCCAGCCTGGAATGGGTGTCCCGCGAACCTGCC
CTGCTGTGCACCTTCCCCAATCCTAGCGCCCCCAGAAAGGACAGCACACTGTCTGCCGTGCCCCAGAGCAGCT
ATCCCCTGCTGGCTAACGGCGTGTGCAAGTGGCCTGGCTGCGAGAAGGTGTTCGAGGAACCCGAGGACTTCC
TGAAGCACTGCCAGGCCGACCATCTGCTGGACGAGAAAGGCAGAGCCCAGTGCCTGCTGCAGCGCGAGATG
GTGCAGTCCCTGGAACAGCAGCTGGTGCTGGAAAAGAAAAGCTGAGCGCCATGCAGGCCCACCTGGCCGG
AAAGATGGCCCTGACAAAAGCCAGCAGCGTGGCCAGCTCCGACAAGGGCAGCTGTTGTATCGTGGCCGCTGG
CAGCCAGGGACCTGTGGTGCCTGCTTGGAGCGGACCTAGAGAGGCCCCCGATAGCCTGTTTGCCGTGCGGAG
ACACCTGTGGGGCAGCCACGGCAACTCTACCTTCCCCGAGTTCCTGCACAACATGGACTACTTCAAGTTCCACA
ACATGAGGCCCCCCTTCACCTACGCCACCCTGATCAGATGGGCCATTCTGGAAGCCCCCGAGAAGCAGCGGAC
CCTGAACGAGATCTACCACTGGTTTACCCGGATGTTCGCCTTCTTCCGGAACCACCCCGCCACCTGGAAGAAC
GCCATCCGGCACAATCTGAGCCTGCACAAGTGCTTCGTGCGGGTGGAAAGCGAGAAGGGCGCCGTGTGGAC
AGTGGACGAGCTGGAATTTCGGAAGAAGCGGTCCCAGAGGCCCAGCCGGTGTAGCAATCCTACACCTGGCCC
TGAGGGCAGAGGAAGTCTGCTAACATGCGGTGACGTCGAGGAGAATCC

FIG. 21

SEQ ID NO. 25 – Amino acid sequence of FOXP3

MPNPRPGKPSAPSLALGPSPGASPSWRAAPKASDLLGARGPGGTFQGRDLRGGAHASSSSLNPMPPSQLQLPTL
PLVMVAPSGARLGPLPHLQALLQDRPHFMHQLSTVDAHARTPVLQVHPLESPAMISLTPPTTATGVFSLKARPGLP
PGINVASLEWVSREPALLCTFPNPSAPRKDSTLSAVPQSSYPLLANGVCKWPGCEKVFEEPEDFLKHCQADHLLDEK
GRAQCLLQREMVQSLEQVEELSAMQAHLAGKMALTKASSVASSDKGSCCIVAAGSQGPVVPAWSGPREAPDSLF
AVRRHLWGSHGNSTFPEFLHNMDYFKFHNMRPPFTYATLIRWAILEAPEKQRTLNEIYHWFTRMFAFFRNHPAT
WKNAIRHNLSLHKCFVRVESEKGAVWTVDELEFRKKRSQRPSRCSNPTPGPEGRGSLLTCGDVEEN

FIG. 22

ENGINEERED REGULATORY T CELL

FIELD OF THE INVENTION

The present invention relates to an engineered regulatory T cell (Treg). In particular, the present invention relates to a Treg comprising a T cell receptor (TCR) which is capable of specifically binding to myelin basic protein (MBP). The present invention further relates to methods for providing an engineered Treg and to methods and uses of said engineered Treg.

BACKGROUND TO THE INVENTION

Many autoimmune and inflammatory central nervous system (CNS) diseases are Involve autoreactive T-cells. For example, Multiple Sclerosis (MS), which is an autoimmune inflammatory demyelinating condition of the central nervous system and is the most common neurological disorder among young adults.

Current treatments for autoimmune and inflammatory CNS diseases generally suppress the immune system. For example, one treatment includes transplantation of bone marrow along with administration of cytostatics and immunosupressive drugs. Autologous haematopoietic stem cell transplantation can have lasting beneficial effects for some patients, but the procedure requires aggressive myelo-ablative conditioning which is associated with substantial toxicity and risk.

Although several disease-modifying treatments (DMTs) have been approved to reduce the frequency of clinical relapses, most patients continue to clinically deteriorate under current therapy schedules. Neither DMTs nor stem cell transplantation can mediate CNS-specific suppression of the immunopathology of autoimmune and inflammatory CNS diseases.

Currently, effective treatments for autoimmune and inflammatory CNS diseases do not exist. Treatment is focused on merely reducing its symptoms, usually by general suppression of the immune system. There is a need for a therapy which specifically targets local immune responses associated with onset and progression of CNS disease.

SUMMARY OF ASPECTS OF THE INVENTION

The present invention is based, at least in part, on the inventors' determination that T cell receptor gene transfer technology can be used to generate antigen-specific Tregs. It has been shown that human antigen-specific Tregs can suppress activated T cells.

In particular, the present inventors have produced MBP-specific Tregs for example, by retroviral transfer of MBP-TCR genes into purified Tregs and by retroviral transfer of MBP-TCR and forkhead box P3 (FOXP3) genes into conventional CD4+ T cells. Without wishing to be bound by theory, these engineered Tregs with TCRs specific for MBP may be used in the suppression of diseases e.g. autoimmune diseases, where local activation of MBP-specific Tregs in the central nervous system (CNS) may suppress CNS pathology as seen in MS and other CNS inflammatory conditions.

Without wishing to be bound by theory, it was unexpected that the present inventors have been able to develop a Treg which suppresses proliferation of pathogenic T cells. It was previously suggested in the field that TCRs in Tregs have higher affinity for self antigen than TCRs in conventional T cells (Pacholczyk and Kern Immunology, 2008. 125(4) 450-458 incorporated herein by reference). It has also been reported that Tregs transduced with an islet-antigen specific TCR were less efficient than Tregs expressing a viral antigen specific TCR. It was suggested that this may be due to Treg-specific TCR requirements—for example a certain affinity requirement. Thus, the Treg repertoire is highly diverse and was thought to have a distinct set of T cell receptors compared to the repertoire of conventional T cells. The present inventors have unexpectedly demonstrated that a MBP-specific TCR isolated from conventional T cells can be successfully expressed in a Treg cell and can produce a functional Treg.

Accordingly, the present invention provides an engineered regulatory T cell (Treg) comprising a T cell receptor (TCR) which is capable of specifically binding to a peptide which comprises at least 90% identity to MBP 111-129 (SEQ ID NO: 3) or a fragment thereof when the peptide is presented by a major histocompatibility complex (MHC) molecule.

The MBP111-129 peptide is known to bind weakly to DRB1*0401. This is in contrast to MBP81-99, for example, which binds with a high affinity to HLA-DR15.

Suitably, the TCR is capable of specifically binding to a peptide which has at least 90% identity to MBP 111-129 (SEQ ID NO: 3) or a fragment thereof when the peptide is presented by a major histocompatibility complex (MHC) molecule.

Suitably, the peptide may be capable of being presented by a HLA-DRB1*0401 molecule.

The TCR may comprise an α chain and a β chain, wherein the α chain and the β chain each comprises three complementarity determining regions (CDRs) and the sequence of each CDR3 is as follows:

```
                                         (SEQ ID NO: 5)
    CDR3α - TVYGGATNKLIFGTGTLLAVQPNIQNPD (SEQ ID NO: 6)
    CDR3β- SARGGSYNSPLHFGNGTRLTVTE
``` or a variant of those sequences having up to three amino acid changes.

The α chain of the TCR may comprise three CDRs having the following amino acid sequences:

```
                                         (SEQ ID NO: 7)
    CDR1α - TISGTDY (SEQ ID NO: 8)
    CDR2α - GLTSN (SEQ ID NO: 9)
    CDR3α - TVYGGATNKLIFGTGTLLAVQPNIQNPD
``` or variants of those sequences having up to three amino acid changes;
and the β chain of the TCR may comprise three CDRs having the following amino acid sequences:

```
                                         (SEQ ID NO: 10)
    CDR1β - DFQATT (SEQ ID NO: 11)
    CDR2β - SNEGSKA (SEQ ID NO: 12)
    CDR3β - SARGGSYNSPLHFGNGTRLTVTE
``` or variants of those sequences having up to three amino acid changes.

The variable region of the α chain of the TCR may comprise an amino acid sequence having at least 80% sequence identity to SEQ ID NO:13, wherein the sequence identity does not include the CDR sequences; and
the variable region of the 13 chain of the TCR may comprise an amino acid sequence having at least 80% sequence identity to SEQ ID NO: 14, wherein the sequence identity does not include the CDR sequences.

The variable region of the α chain of the TCR may comprise an amino acid sequence having at least 80% sequence identity to SEQ ID NO: 19; and
the variable region of the 13 chain of the TCR may comprise an amino acid sequence having at least 80% sequence identity to SEQ ID NO: 21.

The constant region domains of the α chain and 13 chain of the TCR may each comprise an additional cysteine residue, enabling the formation of an extra disulphide bond between the α chain and the β chain. Suitably, the additional disulphide bond reduces mispairing with endogenous TCR chains.

The α chain of the TCR may comprise an amino acid sequence having at least 80% sequence identity to SEQ ID NO: 13; and
the β chain of the TCR may comprise an amino acid sequence having at least 80% sequence identity to SEQ ID NO: 14.

In one aspect, the Treg is derived from a T cell isolated from a subject.

In another aspect, the present invention provides a pharmaceutical composition comprising an engineered Treg according to the invention.

In one aspect, the present invention relates to an engineered Treg or pharmaceutical composition according to the invention for use in treating a disease.

In another aspect, the present invention relates to the use of an engineered Treg or pharmaceutical composition according to the invention in the manufacture of a medicament. In one aspect, there is provided a method for treating or preventing a disease in a subject in need of same which comprises the step of administering an engineered Treg or pharmaceutical composition according to the invention to the subject.

In another aspect, there is provided an engineered Treg or pharmaceutical composition for use, or a use or a method according to the invention, wherein the disease is multiple sclerosis.

In one aspect, there is provided an engineered Treg or pharmaceutical composition for use, or a use or a method according to the invention, wherein the subject is an HLADRB1*0401 positive subject.

In another aspect, there is provided a vector which comprises a nucleic acid sequence which encodes a TCR as defined herein and a nucleic acid sequence which encodes FOXP3.

In one aspect, a kit of polynucleotides or a kit of vectors is provided which comprises a first polynucleotide or vector which comprises a nucleic acid sequence which encodes a TCR as defined herein and a second polynucleotide or vector which comprises a nucleic acid sequence which encodes FOXP3. Suitably, the first and second polynucleotides or vectors are separate.

In one aspect, there is provided a method for producing an engineered Treg according to the invention which comprises the step of introducing into a cell in vitro or ex vivo a polynucleotide encoding a TCR as defined herein.

Suitably the T cell is a natural Treg which expresses FOXP3.

In one aspect, the method further comprises the step of introducing into the cell in vitro or ex vivo a polynucleotide encoding a FOXP3 protein.

Suitably the cell is a T cell.

Suitably the T cell is a 'conventional' T cell.

In one aspect of a method of the invention, the step of introducing the polynucleotide encoding a TCR and the polynucleotide encoding FOXP3 are performed sequentially, separately or simultaneously.

In another aspect of a method of the invention, the polynucleotide encoding a TCR and the polynucleotide encoding FOXP3 are introduced to the cell using the vector of the invention.

These data show that TCR-transduced Treg and TCR-FOXP3 converted Tconv are hyporesponsive to cognate peptide.

Figure 10:
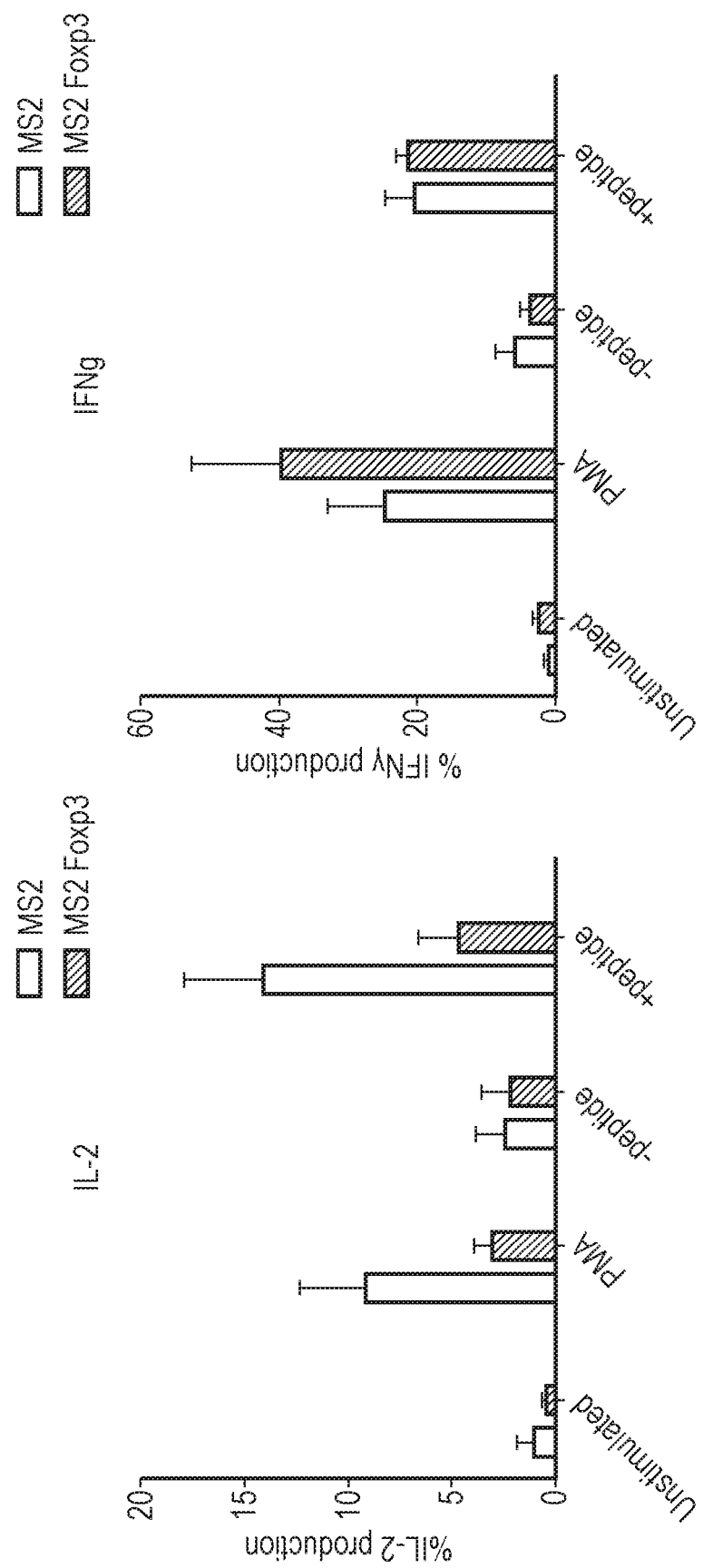

FIG. 10—shows IL-2 and IFNγ production from cells expressing the MS2 TCR and production from T cells expressing MS2 TCR and FOXP3 (n=3). Conventional T cells (T conv) transduced with TCR and TCR+FOXP3 produce less IL-2 than conventional cells transduced with TCR alone.

Figure 11:
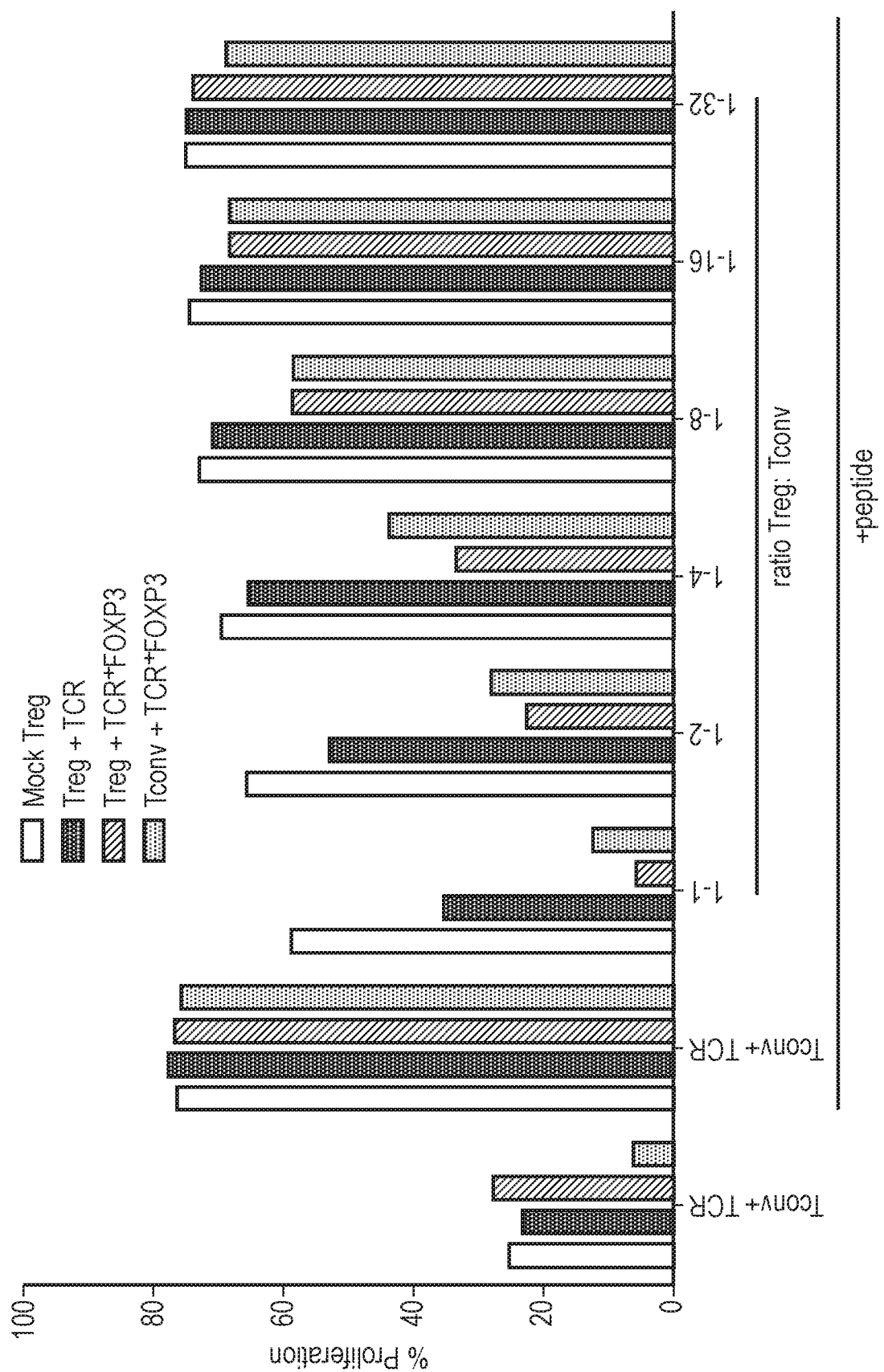

FIG. 11—TCR transduced T conv were stained with CFSE and cultured with or without peptide-pulsed irradiated APC at a ratio of 1 Tconv:0.01 APC for 4 days. Mock Treg (bar on the furthest left), MBP TCR-transduced Treg (second bar from the left), MBP TCR-FOXP3-transduced Treg (third bar from the left) and MBP TCR-FOXP3-transduced Tconv (fourth bar from the left in each group) were added in the indicated ratios. Proliferation was determined by analysing dilution of CFSE-stained Tconv (B). These data show that TCR-transduced Treg suppress T cell responses in an antigen-specific manner.

Figure 12:
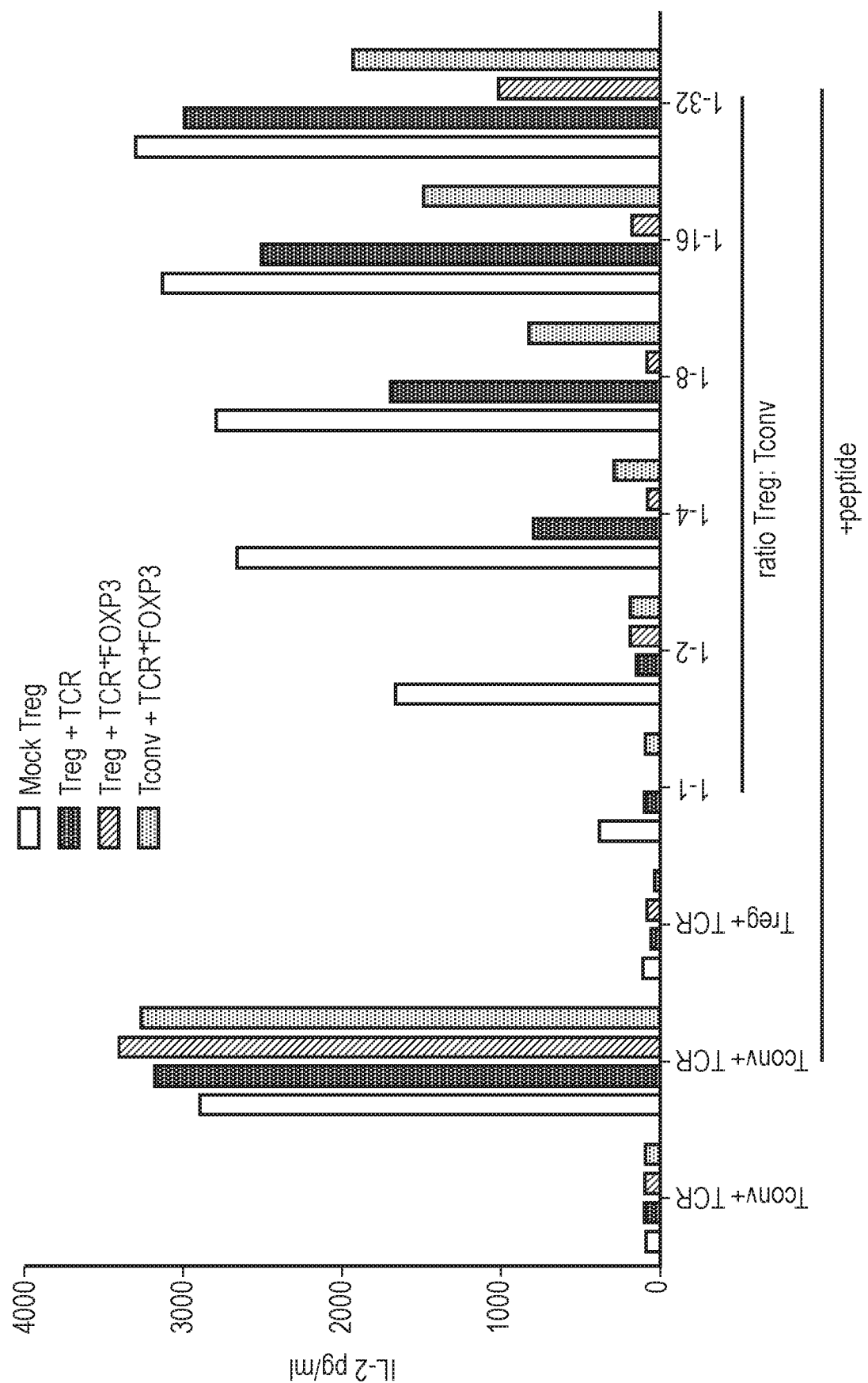

FIG. 12—TCR transduced T conv were stained with CFSE and cultured with or without peptide-pulsed irradiated APC at a ratio of 1 Tconv:0.01 APC for 4 days. Mock Treg (bar on the furthest left), MBP TCR-transduced Treg (second bar from the left), MBP TCR-FOXP3-transduced Treg (third bar from the left) and MBP TCR-FOXP3-transduced Tconv (fourth bar from the left in each group) were added in the indicated ratios. Supernatants were collected and assayed for IL-2 by ELISA. These data show that TCR-transduced Treg suppress T cell responses in an antigen-specific manner.

FIG. 13—shows the sequence of SEQ ID NO: 18, the nucleotide sequence of the alpha chain V-region of MS2.3C8-alpha-variable(Va26-2) domain.

FIG. 14—shows the sequence of SEQ ID NO: 19, the amino acid sequence of the alpha chain V-region of MS2.3C8-alpha-variable(Va26-2) domain.

FIG. 15—shows the amino acid sequence of SEQ ID NO: 13, the human a V-region and murine constant-region.

FIG. 16—shows the sequence of SEQ ID NO: 20, the nucleotide sequence of the beta chain human V-region of the MS2.3C8-beta-variable domain.

FIG. 17—shows the amino acid sequence of SEQ ID NO: 21, the nucleotide sequence of the beta chain human V-region of the MS2.3C8-beta-variable domain.

FIG. 18—shows the sequence of SEQ ID NO: 14, the polypeptide sequence of the human β V-region and murine C-region.

FIG. 19—shows the sequence of SEQ ID NO: 22, MS2.3C8-alpha-variable amino acid sequence excluding CDR sequences.

FIG. 20—shows the sequence of SEQ ID NO: 23, MS2.3C8-beta-variable amino acid sequence excluding CDR sequences.

FIG. 21—shows the nucleic acid sequence of SEQ ID NO: 24, which encodes FOXP3.

FIG. 22—shows the amino acid sequence of SEQ ID NO: 25, FOXP3.

Figure 23A:
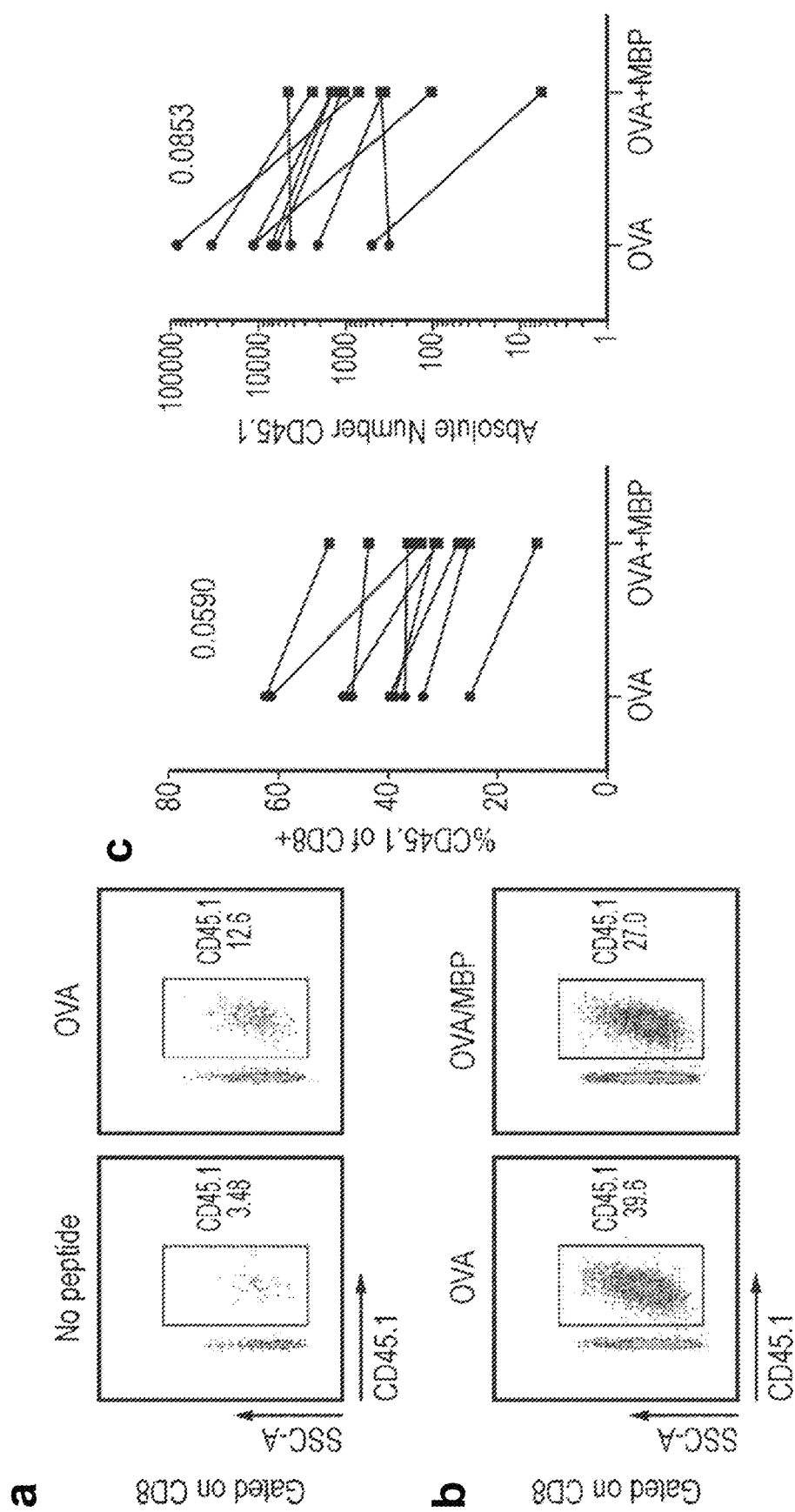
Figure 23B:
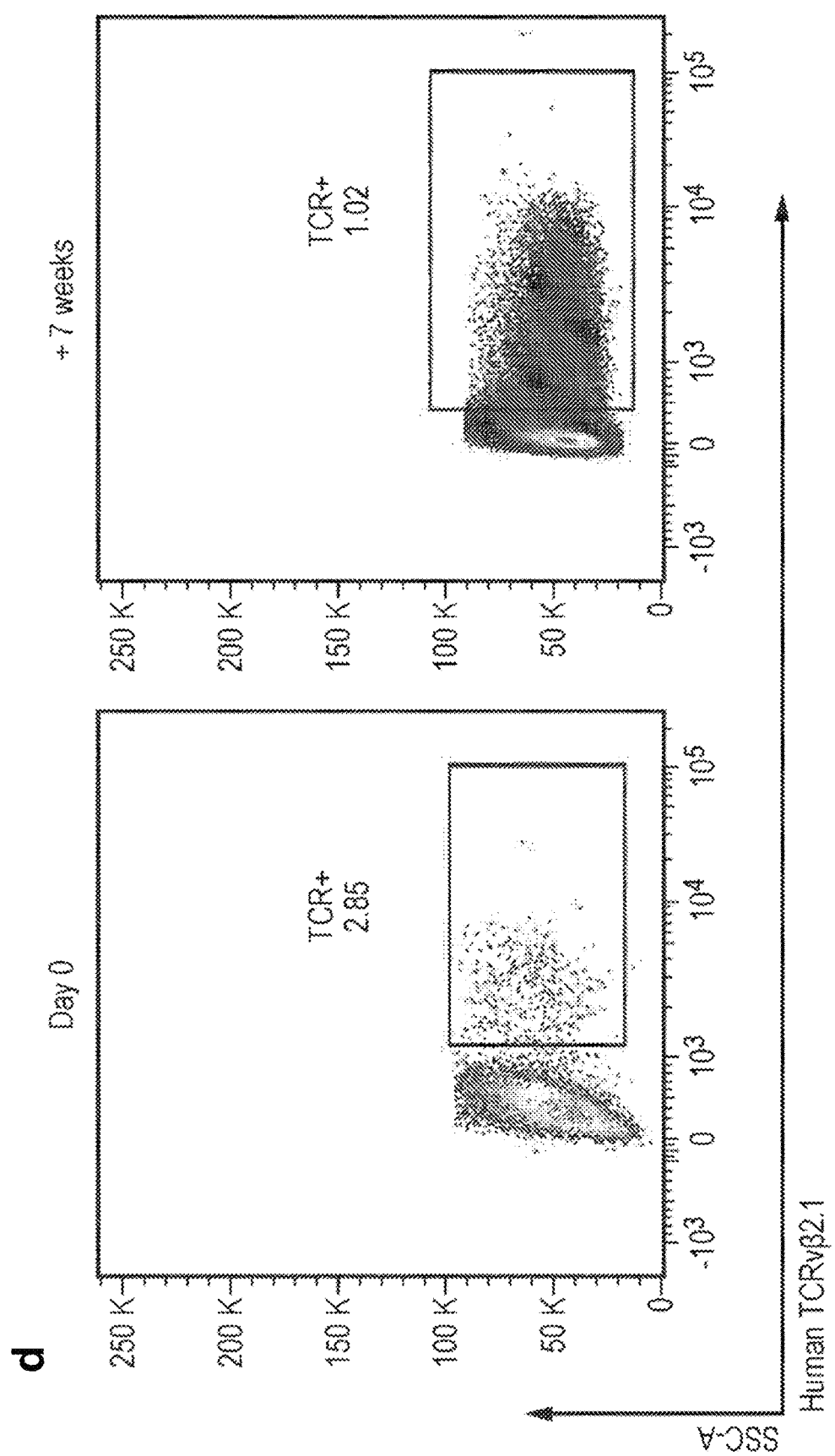
Figure 23C:
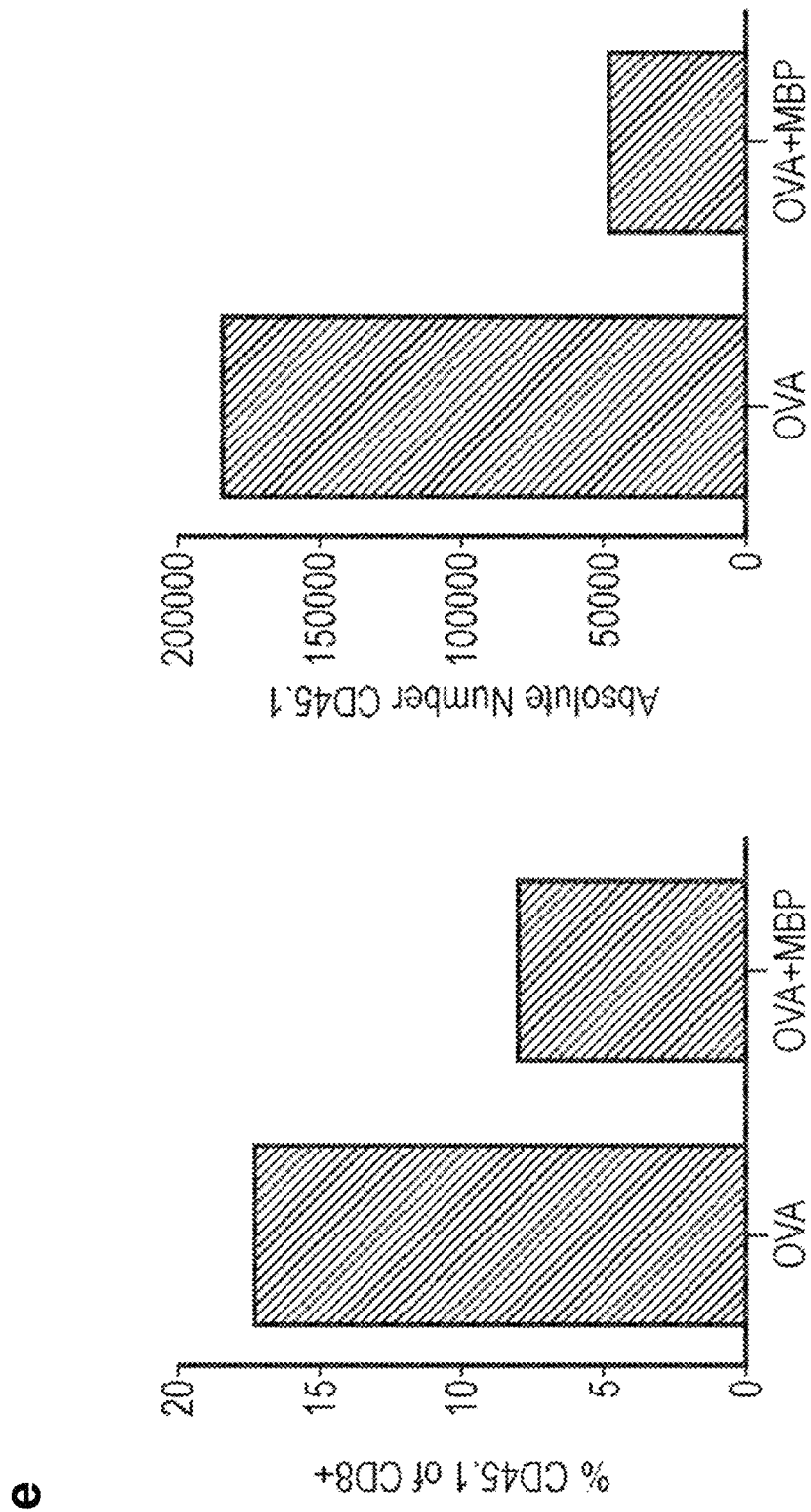

FIG. 23A-23C—CD4+CD25+Treg were isolated from lymph nodes and splenocytes of HLA-DRB*0401 transgenic mice by bead sort. Treg were transduced with TCR+ murine FOXP3. Transduced cells and equivalent numbers of CD45.1+OTI transgenic T cells (specific for ovalbumin) were injected into HLA-DRB*0401 transgenic hosts conditioned with 4Gy irradiation. After 7 days mice were injected sub-cutaneously in the right or left flank with 30ug ovalbumin (OVA) or 30ug of OVA and 30ug of human myelin basic protein (MBP) in incomplete Freud's adjuvant. In FIG. 23A, paired FACS plots (a and b) show OTI cells identified by CD45.1 in the right and left inguinal lymph nodes of the same mouse. In paired FACS plots A, the left plot shows the data from an uninjected flank (no peptide) and the right shows data from the flank injected with OVA peptide. In paired FACS plots b, the left plot shows the data from the flank injected with OVA and the right shows data from the flank injected with OVA+MBP peptides C. In paired panels c, cumulative data from 3 independent experiments showing % CD45.1+cells (left panel) and absolute number of CD45.1 cells (right panel) in the inguinal lymph node of the flank that received OVA or OVA+MBP (n=9). In FIG. 23B, paired FACS plots d show data of transduced Treg that were positive for TCR staining at day 0 (left plot) and after 7 weeks (right plot). In FIG. 23C, graph e shows % CD45.1+ cells in the CD8+population (left panel) and absolute number of CD45.1 cells (right panel) 7 weeks post-administration.

DETAILED DESCRIPTION

Myelin Basic Protein (MBP) Peptides

Myelin basic protein is important in the process of myelination of nerves and is found in the myelin sheath of cells in the nervous system such as oligodendrocytes and Schwann cells. MBP transcripts are also found in the bone marrow and the immune system. One function of the myelin sheath is to increase the velocity of axonal impulse conduction. MBP helps to maintain the correct structure of myelin and interacts with lipids in the myelin membrane. MBP is known to localise to the CNS and to various haematopoietic cells.

MBP has been implicated in the pathogenesis of demyelinating diseases, such as multiple sclerosis (MS). Studies have demonstrated a role for antibodies against MBP in the pathogenesis of MS.

In one aspect, an illustrative amino acid sequence of MBP comprises the sequence with UniProtKB accession P02686-1, shown as SEQ ID NO: 1:

```
                                          (SEQ ID NO: 1)
MGNHAGKRELNAEKASTNSETNRGESEKKRNLGELSRTTSEDNEVFGEADA

NQNNGTSSQDTAVTDSKRTADPKNAWQDAHPADPGSRPHLIRLFSRDAPGR

EDNTFKDRPSESDELQTIQEDSAATSESLDVMASQKRPSQRHGSKYLATAS

TMDHARHGFLPRHRDTGILDSIGRFFGGDRGAPKRGSGKDSHHPARTAHYG

SLPQKSHGRTQDENPVVHFFKNIVTPRTPPPSQGKGRGLSLSRFSWGAEGQ

RPGFGYGGRASDYKSAHKGFKGVDAQGTLSKIFKLGGRDSRSGSPMARR.
```

In one aspect, an illustrative amino acid sequence of MBP comprises SEQ ID NO: 1 or a variant or fragment thereof.

In one aspect, the amino acid sequence of MBP comprises SEQ ID NO: 1.

In one aspect, the amino acid sequence of MBP is SEQ ID NO: 1.

Suitably, an illustrative amino acid sequence of MBP may be an isoform of UniProtKB accession P02686-1, such as UniProtKB accession P02686-5. Isoform P02686-5 differs from the canonical sequence shown above in SEQ ID NO:1 as follows, amino acid residues 1-133 are missing.

UniProtKB accession P02686-5 is shown as SEQ ID NO: 26:

(SEQ ID NO: 26)
MASQKRPSQRHGSKYLATASTMDHARHGFLPRHRDTGILDSIGRFFGGDRG

APKRGSGKDSHHPARTAHYGSLPQKSHGRTQDENPVVHFFKNIVTPRTPPP

SQGKGRGLSLSRFSWGAEGQRPGFGYGGRASDYKSAHKGFKGVDAQGTLSK

IFKLGGRDSRSGSPMARR.

In one aspect, the present invention provides an engineered Treg comprising a TCR which is capable of specifically binding to a peptide which comprises at least 90% identity to MBP 100-140: PPSQGKGRGLSLSRFSWGAE-GQRPGFGYGGRASDYKSAHKG (SEQ ID NO: 2) or a fragment thereof when the peptide is presented by a major histocompatibility complex (MHC) molecule.

Suitably, the TCR is capable of specifically binding to a peptide which has at least 90% identity to MBP 100-140: PPSQGKGRGLSLSRFSWGAEGQRPGFGYGGR-ASDYKSAHKG (SEQ ID NO: 2) or a fragment thereof when the peptide is presented by a major histocompatibility complex (MHC) molecule.

Unless otherwise stated, MBP XXX-XXX as used herein refers to the numbering used in Muraro et al., JCI 1997; 100, 2, 339-349, incorporated herein by reference.

One may determine whether a peptide is capable of being presented by a MHC molecule and recognised by a T cell using methods available in the art. For example, an assay may comprise co-culturing antigen presenting cells (APCs) expressing the MHC:peptide complex to be tested with T cells comprising the TCR defined herein. T cell proliferation may then be measured as an indication of successful presentation of the peptide (for example by carboxyfluorescein succinimidyl ester (CFSE) assay). Alternatively, effector cytokine production may also be measured.

In one aspect, the MBP peptide comprises a sequence which comprises at least 90% identity to MBP 100-140: PPSQGKGRGLSLSRFSWGAEGQRPGFGYGGR-ASDYKSAHKG (SEQ ID NO: 2) or a fragment thereof. Suitably, the MBP peptide has at least 95%, 97%, 98% or 99% identity to MBP 100-140 (SEQ ID NO: 2) or a fragment thereof.

Suitably, the MBP peptide comprises a sequence which has at least 90% identity to MBP 100-140: PPSQGKGR-GLSLSRFSWGAEGQRPGFGYGGRASDYKSAHKG (SEQ ID NO: 2) or a fragment thereof. Suitably, the MBP peptide has at least 95%, 97%, 98% or 99% identity to MBP 100-140 (SEQ ID NO: 2) ora fragment thereof.

The MBP peptide may be mutated compared to MBP 100-140 (SEQ ID NO: 2). For example, the MBP peptide may be mutated by amino acid insertion, deletion or substitution, so long as the modified MBP peptide retains the MHC binding specificity of the unmodified peptide, and is capable of being presented to a T cell. The MBP peptide may, for example have 3, 2, 1 or 0 mutations relative to MBP 100-140 (SEQ ID NO: 2). Suitably the MBP peptide may, for example have 3, 2, 1 or 0 conservative amino acid substitutions relative to MBP 100-140 (SEQ ID NO: 2). Suitably the MBP peptide may, for example have 3, 2, 1 or 0 insertions relative to MBP 100-140 (SEQ ID NO: 2). Suitably the MBP peptide fragment may, for example have 3, 2, 1 or 0 deletions relative to MBP 100-140 (SEQ ID NO: 2).

As used herein "specifically binding" means that the TCR binds to the peptide but does not bind to other peptides, or binds at a lower affinity to other peptides.

The binding affinity between two molecules, e.g. a TCR and a peptide, or fragment thereof, may be quantified for example, by determination of the dissociation constant (KD). The KD can be determined by measurement of the kinetics of complex formation and dissociation between the TCR and the peptide, e.g. by the surface plasmon resonance (SPR) method (Biacore™). The rate constants corresponding to the association and the dissociation of a complex are referred to as the association rate constants ka (or kon) and dissociation rate constant kd. (or koff), respectively. KD is related to ka and kd through the equation KD=kd/ka.

Binding affinities associated with different molecular interactions, e.g. comparison of the binding affinity of different TCRs and peptides, may be compared by comparison of the KD values for the individual TCR/peptide complexes.

The peptide may be capable of being presented by any Human Leukocyte Antigen—antigen D Related (HLA-DR). For example, the peptide may be capable of being presented by a HLA-DR4, HLA-DR2, HLA-DR15, or HLA-DR16.

In one aspect, the peptide is capable of being presented by a HLA-DR4.

In one aspect, the peptide is capable of being presented by a HLA-DRB1*0401 molecule.

In one aspect, the peptide has at least 90% identity to MBP 111-129: LSRFSWGAEGQRPGFGYGG (SEQ ID NO:3). The MBP peptide may be mutated compared to MBP 111-129 (SEQ ID NO: 3). For example, the MBP peptide may be mutated by amino acid insertion, deletion or substitution, so long as the modified MBP peptide retains the MHC binding specificity of the unmodified peptide, and is capable of being presented to a T cell. The peptide may, for example have 3, 2, 1 or 0 mutations relative to MBP 111-129 (SEQ ID NO: 3). Suitably the peptide may, for example have 3, 2, 1 or 0 conservative mutations relative to MBP 111-129 (SEQ ID NO: 3). Suitably the peptide may, for example have 3, 2, 1 or 0 insertions relative to MBP 111-129 (SEQ ID NO: 3). Suitably the MBP peptide fragment may, for example have 3, 2, 1 or 0 deletions relative to MBP 111-129 (SEQ ID NO: 3). Suitably, the MBP 111-129 (SEQ ID NO: 3) peptide fragment retains the MHC binding specificity of the MBP 111-129 (SEQ ID NO: 3) peptide, and is capable of being presented to a T cell.

In one aspect, the peptide has at least 85% identity to MBP 116-123: WGAEGQRP (SEQ ID NO: 4).

In one aspect, the peptide has one, two or three amino acid substitutions, insertions or deletions compared to MBP 116-123: WGAEGQRP (SEQ ID NO: 4). Suitably the peptide has one, two or three conservative amino acid substitution compared to MBP 116-123: WGAEGQRP (SEQ ID NO: 4). Suitably the peptide has one, two or three insertions compared to MBP 116-123: WGAEGQRP (SEQ ID NO: 4). Suitably the MBP peptide fragment has one, two or three deletions compared to MBP 116-123: WGAEGQRP (SEQ ID NO: 4). Suitably, the MBP 116-123 (SEQ ID NO: 4) peptide fragment retains the MHC binding specificity of the MBP 116-123 (SEQ ID NO: 4) peptide, and is capable of being presented to a T cell.

In one aspect, the peptide comprises MBP 116-123: WGAEGQRP (SEQ ID NO: 4).

In one aspect, the peptide is MBP 116-123: WGAEGQRP (SEQ ID NO: 4).

T Cell Receptor (Tcr)

The variable domain of both the TCR α-chain and β-chain have three hypervariable or complementarity determining regions (CDRs). CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. Framework regions (FRs) are positioned between the CDRs. These regions provide the structure of the TCR variable region.

The TCR of the present invention comprises sufficient of the variable domains thereof to be able to interact with its peptide/MHC complex. Such interaction can be measured using a Biacore™ instrument, for example. Suitably the TCR may interact with HLADRB1*0401.

The repertoire of TCR variable regions is generated by combinatorial joining of variable (V), joining (J) and diversity (D) genes; and by N region diversification (nucleotides inserted by the enzyme deoxynucleotidyl-transferase).

α chains are formed from recombination events between the V and J segments. β chains are formed from recombination events involving the V, D and J segments.

The human TCRα locus, which also includes the TCRδ locus, is located on chromosome 14 (14q11.2). The TCRβ locus is located on chromosome 7 (7q34). The variable region of the TCRα chain is formed by recombination between one of 46 different Vα (variable) segments and one of 58 Jα (joining) segments (Koop et al.; 1994; Genomics; 19: 478-493 incorporated herein by reference). The variable region of a TCRβ chain is formed from recombination between 54 Vβ, 14 Jβ and 2 Dβ (diversity) segments (Rowen et al.; 1996; Science; 272:1755-1762 incorporated herein by reference).

The V and J (and D as appropriate) gene segments for each TCR chain locus have been identified and the germline sequence of each gene is known and annotated (for example see Scaviner & Lefranc; 2000; Exp Clin Immunogenet; 17:83-96 and Folch & Lefranc; 2000; Exp Clin Immunogenet; 17:42-54, incorporated herein by reference).

FR1, CDR1, FR2, CDR2, FR3 and CDR3 of the α chain of natural TCRs are encoded by the Vα gene. FR1, CDR1, FR2, CDR2 and FR3 of the β chain of natural TCRs are encoded by the Vβ gene.

As the germline sequence of each variable gene is known in the art (see Scaviner & Lefranc; as above and Folch & Lefranc; supra) the Vα and/or Vβ of a particular TCR can be sequenced and the germline V segment which is utilised in the TCR can be identified (see, for example, Hodges et al.; 2003; J Clin Pathol; 56:1-11, Zhou et al.; 2006; Laboratory Investigation; 86; 314-321, incorporated herein by reference).

The present invention provides an engineered Treg comprising an engineered T cell receptor.

In one aspect, the invention provides an engineered Treg comprising a TCR which is capable of specifically binding to a peptide which comprises at least 90% identity to MBP 100-140 (SEQ ID NO: 2) or a fragment thereof when the peptide is presented by a major histocompatibility complex (MHC) molecule.

Suitably, the invention provides an engineered Treg comprising a TCR which is capable of specifically binding to a peptide which has at least 90% identity to MBP 100-140 (SEQ ID NO: 2) or a fragment thereof when the peptide is presented by a major histocompatibility complex (MHC) molecule.

In one aspect, the TCR comprises an α chain and a β chain, wherein the α chain and the β chain each comprises three complementarity determining regions (CDRs) and the sequence of each CDR3 is as follows:

```
                                            (SEQ ID NO: 5)
CDR3α - TVYGGATNKLIFGTGTLLAVQPNIQNPD (SEQ ID NO: 6)
CDR3β - SARGGSYNSPLHFGNGTRLTVTE
``` or a variant of those sequences having up to three amino acid changes.

In one aspect, the α chain of the TCR comprises three CDRs having the following amino acid sequences:

```
                                            (SEQ ID NO: 7)
CDR1α - TISGTDY (SEQ ID NO: 8)
CDR2α - GLTSN (SEQ ID NO: 9)
CDR3α - TVYGGATNKLIFGTGTLLAVQPNIQNPD
``` or variants of those sequences having up to three amino acid changes;
and wherein the β chain of the TCR comprises three CDRs having the following amino acid sequences:

```
                                            (SEQ ID NO: 10)
CDR1β - DFQATT (SEQ ID NO: 11)
CDR2β - SNEGSKA (SEQ ID NO: 12)
CDR3β - SARGGSYNSPLHFGNGTRLTVTE
``` or variants of those sequences having up to three amino acid changes.

Suitably the amino acid change in a CDR is a conservative substitution, insertion or deletion. Preferably the amino acid change is a conservative substitution.

In one aspect, the variable region of the α chain of the TCR comprises an amino acid sequence having at least 80% sequence identity to SEQ ID NO:19, and the variable region of the β chain of the TCR comprises an amino acid sequence having at least 80% sequence identity to SEQ ID NO: 21, wherein the sequence identity does not include the CDR sequences. Suitably the CDR sequences are as disclosed herein. Suitably, the variable region of the α chain of the TCR comprises an amino acid sequence having at least 80%, 85%, 90%, 95% or 97% sequence identity to SEQ ID NO:19, and the variable region of the β chain of the TCR comprises an amino acid sequence having at least 80%, 85%, 90%, 95%, or 97% sequence identity to SEQ ID NO: 21.

Suitably, the variable region of the α chain of the TCR comprises an amino acid sequence may have at least 85% sequence identity to SEQ ID NO:19, and the variable region of the β chain of the TCR comprises an amino acid sequence having at least 85% sequence identity to SEQ ID NO: 21, wherein the sequence identity does not include the CDR sequences. Suitably, the variable region of the α chain of the TCR comprises an amino acid sequence may have at least 90% sequence identity to SEQ ID NO:19, and the variable region of the β chain of the TCR comprises an amino acid sequence having at least 90% sequence identity to SEQ ID NO: 21, wherein the sequence identity does not include the CDR sequences. Suitably, the variable region of the α chain of the TCR comprises an amino acid sequence may have at least 95% sequence identity to SEQ ID NO:19 and the variable region of the β chain of the TCR comprises an amino acid sequence having at least 95% sequence identity to SEQ ID NO: 21, wherein the sequence identity does not include the CDR sequences. Suitably, the variable region of the α chain of the TCR comprises an amino acid sequence may have at least 97% sequence identity to SEQ ID NO:19 and the variable region of the β chain of the TCR comprises an amino acid sequence having at least 97% sequence identity to SEQ ID NO: 21, wherein the sequence identity does not include the CDR sequences. Suitably, the variable region of the α chain of the TCR comprises an amino acid sequence set fort in SEQ ID NO:19 and the variable region of the β chain of the TCR comprises an amino acid sequence set forth in SEQ ID NO: 21, wherein the sequence identity does not include the CDR sequences.

In another aspect, the variable region of the α chain of the TCR comprises an amino acid sequence having at least 80% sequence identity to SEQ ID NO: 19; and the variable region of the β chain of the TCR comprises an amino acid sequence having at least 80% sequence identity to SEQ ID NO: 21. Suitably, the variable region of the α chain of the TCR comprises an amino acid sequence having at least 85% sequence identity to SEQ ID NO: 19; and the variable region of the β chain of the TCR comprises an amino acid sequence having at least 85% sequence identity to SEQ ID NO: 21. Suitably, the variable region of the α chain of the TCR comprises an amino acid sequence having at least 90% sequence identity to SEQ ID NO: 19; and the variable region of the β chain of the TCR comprises an amino acid sequence having at least 90% sequence identity to SEQ ID NO: 21. Suitably, the variable region of the α chain of the TCR comprises an amino acid sequence having at least 95% sequence identity to SEQ ID NO: 19; and the variable region of the β chain of the TCR comprises an amino acid sequence having at least 95% sequence identity to SEQ ID NO: 21. Suitably, the variable region of the α chain of the TCR comprises an amino acid sequence having at least 97% sequence identity to SEQ ID NO: 19; and the variable region of the β chain of the TCR comprises an amino acid sequence having at least 97% sequence identity to SEQ ID NO: 21.

In one aspect, the α chain of the TCR comprises an amino acid sequence having at least 80% sequence identity to SEQ ID NO: 13; and the β chain of the TCR comprises an amino acid sequence having at least 80% sequence identity to SEQ ID NO: 14.

Suitably, the α chain of the TCR comprises an amino acid sequence having at least 85% sequence identity to SEQ ID NO: 13; and the β chain of the TCR comprises an amino acid sequence having at least 85% sequence identity to SEQ ID NO: 14. Suitably, the α chain of the TCR comprises an amino acid sequence having at least 90% sequence identity to SEQ ID NO: 13; and the β chain of the TCR comprises an amino acid sequence having at least 90% sequence identity to SEQ ID NO: 14. Suitably, the α chain of the TCR comprises an amino acid sequence having at least 95% sequence identity to SEQ ID NO: 13; and the β chain of the TCR comprises an amino acid sequence having at least 95% sequence identity to SEQ ID NO: 14. Suitably, the α chain of the TCR comprises an amino acid sequence having at least 97% sequence identity to SEQ ID NO: 13; and the β chain of the TCR comprises an amino acid sequence having at least 97% sequence identity to SEQ ID NO: 14.

In another aspect, the constant region domains of the α chain and β chain of the TCR each comprise an additional cysteine residue, enabling the formation of an extra disulphide bond between the α chain and the β chain.

Suitably, residue 48 in the constant alpha chain is converted from a threonine to a cysteine and residue 57 of the constant beta chain is converted from a serine to a cysteine for the formation of the additional disulphide bond.

Suitably, the TCR is codon optimised.

Suitably, the TCR is codon optimised for expression in a mouse.

In one aspect the constant domains employed in the TCR are murine sequences.

Suitably the constant regions have been murinised. For example, both the constant-alpha and the constant-beta domains have been murinised.

In another aspect, the TCR is codon optimised for expression in a human. Suitably, the constant domains employed in the TCR are human sequences.

In one aspect the TCR may comprise, for example, human variable regions and murine constant regions.

The present TCR may comprise one or more amino acid residues as defined herein which is not encoded by the germline Vα or Vβ gene. In other words, the TCR may comprise part of an α chain and/or β chain which comprises an altered amino acid residue at one or more of the positions described herein, compared to the corresponding α chain and/or β chain as encoded by the unaltered germline Vα or Vβ gene.

The amino acid residues identified herein as framework (FR) or complementarity-determining regions (CDRs) are identified according to the International ImMunoGeneTics information system' (IMGT). This system is well known in the art (Lefrance et al.; 2003; Dev Comp Immunol; 27: 55-77) and is based on the high conservation of the structure of the variable region. The numbering takes into account and combines the definition of the FR and CDRs, structural data from X-ray diffraction studies and the characterization of the hypervariable loops.

The delimitations of the FR and CDR regions are defined within the IMGT numbering system. The FR1 region comprises positions 1-26 (25-26 amino acids, depending on the V-GENE group or subgroup) with 1st-CYS at position 23. The FR2 region comprises positions 39-55 (16-17 amino acids) with a conserved TRP at position 41. The FR3 region comprises positions 66-104 (36-39 amino acids, depending on the VGENE group or subgroup) with a conserved hydrophobic amino acid at position 89 and the 2nd-CYS at position 104. Residue 1 of the IGMT numbering system is the first residue in FR1. Residue 104 of the IGMT numbering system is the last residue in FR3.

Methods suitable for generating a TCR according to the present invention are known in the art.

For example mutagenesis may be performed to alter specific nucleotides in a nucleic acid sequence encoding the TCR. Such mutagenesis will alter the amino acid sequence of the TCR so that it comprises one or more of the amino acid residues as described herein.

An example of a mutagenesis method is the Quikchange method (Papworth et al.; 1996; Strategies; 9(3); 3-4). This method involves the use of a pair of complementary mutagenic primers to amplify a template nucleic acid sequence in a thermocycling reaction using a high-fidelity non-strand-displacing DNA polymerase, such as pfu polymerase.

The terms "one or more" or "at least one" as used herein may include one, two, three, four, five, six, seven, eight, nine, ten, eleven, twelve, thirteen, fourteen, fifteen, sixteen, seventeen, eighteen, nineteen, twenty or more amino acid residues as described herein.

The term "two or more" as used herein may include two, three, four, five, six, seven, eight, nine, ten, eleven, twelve, thirteen, fourteen, fifteen, sixteen, seventeen, eighteen, nineteen, twenty or more amino acid residues as described herein.

Conservative Substitution

Suitably, the amino acid residues present at a given position in the present invention may be defined as a residue which is biochemically similar to the amino acids recited for the given SEQ ID NOs.

Amino acids with similar biochemical properties may be defined as amino acids which can be substituted via a conservative substitution.

Conservative amino acid substitutions may be made on the basis of similarity in polarity, charge, solubility, hydrophobicity, hydrophilicity, and/or the amphipathic nature of the residues as long as high expression of the TCR is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to Table 3 below. Amino acids in the same block in the second column and preferably in the same line in the third column may be substituted for each other:

TABLE 3

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) i.e. like-for-like substitution such as basic for basic, acidic for acidic, polar for polar etc.

Unless otherwise explicitly stated herein by way of reference to a specific, individual amino acid, amino acids may be substituted using conservative substitutions as recited below.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in Table 3.

Sequences

The present invention further provides a nucleotide sequence encoding a TCR α chain and/or β chain described herein. In one aspect, a nucleotide sequence encoding a TCR described herein may be introduced into a cell.

As used herein, the term "introduced" refers to methods for inserting foreign DNA into a cell. As used herein the term introduced includes both transduction and transfection methods. Transfection is the process of introducing nucleic acids into a cell by non-viral methods. Transduction is the process of introducing foreign DNA into a cell via a viral vector.

As used herein, the terms "polynucleotide" and "nucleic acid" are intended to be synonymous with each other. The nucleic acid sequence may be any suitable type of nucleotide sequence, such as a synthetic RNA/DNA sequence, a cDNA sequence or a partial genomic DNA sequence.

The term "polypeptide" as used herein is used in the normal sense to mean a series of residues, typically L-amino acids, connected one to the other typically by peptide bonds between the α-amino and carboxyl groups of adjacent amino acids. The term is synonymous with "protein".

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The polynucleotide may be in isolated or recombinant form. It may be incorporated into a vector and the vector may be incorporated into a host cell. Such vectors and suitable hosts form yet further aspects of the present invention.

The polynucleotide may be double or single stranded, and may be RNA or DNA.

The polynucleotide may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. Suitably the polynucleotide may be codon optimised for expression in a murine model of disease. Suitably, the polynucleotide may be codon optimised for expression in a human subject.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation may also involve the removal of mRNA instability motifs and cryptic splice sites.

The polynucleotide may comprise a nucleic acid sequence which enables both a nucleic acid sequence encoding an α chain and a nucleic acid sequence encoding a β chain to be expressed from the same mRNA transcript.

For example, the polynucleotide may comprise an internal ribosome entry site (IRES) between the nucleic acid sequences which encode the α chain and the β chain. An IRES is a nucleotide sequence that allows for translation initiation in the middle of a mRNA sequence.

The polynucleotide may comprise a nucleic acid sequence encoding an α chain and a nucleic acid sequence a β chain linked by an internal self-cleaving sequence.

The internal self-cleaving sequence may be any sequence which enables the polypeptide comprising the α chain and the polypeptide comprising the β chain to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide, various models have been proposed for to account for the "cleavage" activity: proteolysis by a host-cell proteinase, autoproteolysis or a translational effect (Donnelly et al (2001) J. Gen. Virol. 82:1027-1041 incorporated herein by reference). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

A variant can be considered in terms of similarity (i.e. amino acid residues having similar chemical properties/functions), preferably a variant is expressed in terms of sequence identity.

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387 incorporated herein by reference). Examples of other software than can perform sequence comparisons include, but are not limited to, the BLAST package (see Ausubel et al., 1999 ibid—Chapter 18), FASTA (Atschul et al., 1990, J. Mol. Biol., 403-410 incorporated herein by reference) and the GENEWORKS suite of comparison tools. Both BLAST and FASTA are available for offline and online searching (see Ausubel et al., 1999 ibid, pages 7-58 to 7-60 incorporated herein by reference). However it is preferred to use the GCG Bestfit program.

In one embodiment, the sequence identity is determined across the entirety of the sequence. In one embodiment, the sequence identity is determined across the entirety of the candidate sequence being compared to a sequence recited herein.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % sequence identity. The software typically does this as part of the sequence comparison and generates a numerical result.

The term "variant" according to the present invention includes any substitution of, variation of, modification of, replacement of, deletion of or addition of one (or more) amino acids from or to the sequence providing the resultant amino acid sequence retains substantially the same activity as the unmodified sequence. For example, conservative amino acid substitutions may be made. As used herein, a variant polypeptide is taken to include a polypeptide comprising an amino acid sequence which is at least 70, 80, 85, 90, 95, 98 or 99% identical to a sequence shown herein.

In one aspect, the variant maintains the function of the parent sequence.

In one aspect, a cell according to the invention a nucleotide sequence which encodes a FOXP3 protein has also been introduced to the cell.

In one aspect, the cell, engineered Treg or pharmaceutical composition of the present invention may comprise a nucleic acid sequence which encodes a FOXP3 protein, suitably the nucleic acid sequence encodes an amino acid sequence shown as SEQ ID NO: 17 or an amino acid sequence which is at least 80, 85, 90, 95, 98 or 99% identical, preferably at least 95 or 99% identical to a sequence shown herein as SEQ ID NO: 17.

The nucleic acid encoding the TCR and/or FOXP3 may comprise a leader sequence upstream of the initiation codon. This sequence may regulate translation of a transcript. By ay of example, suitable leader sequences for use in the present invention are:

```
                                   (SEQ ID NO: 15)
MKLVTSITVLLSLGIMG
and
                                   (SEQ ID NO: 16)
MLLLLLLLGPGISLLLPGSLAGSGL.
```

In a further aspect the present invention provides a kit of nucleic acid sequences comprising: a first nucleic acid sequence which encodes a TCR as defined herein and a second nucleic acid which encodes FOXP3.

Vector

The present invention also provides a vector comprising a nucleotide sequence encoding a TCR as described herein. Suitably, the vector may additionally comprise a nucleotide sequence encoding a forkhead box P3 (FOXP3) polypeptide. In one aspect, there is provided a kit of vectors which comprises one or more nucleic acid sequence(s) of the invention such as a nucleic acid encoding a TCR as defined herein and a nucleic acid encoding FOXP3.

FOXP3 is a member of the FOX protein family of transcription factors and functions as a master regulator of the regulatory pathway in the development and function of regulatory T cells.

Suitably, the FOXP3 polypeptide is from a human e.g. the UniProtKB accession:

```
Q9BZS1:
                                   (SEQ ID NO: 17)
MPNPRPGKPSAPSLALGPSPGASPSWRAAPKASDLLGARGPGGTFQGRDLR

GGAHASSSSLNPMPPSQLQLPTLPLVMVAPSGARLGPLPHLQALLQDRPHF

MHQLSTVDAHARTPVLQVHPLESPAMISLTPPTTATGVFSLKARPGLPPGI

NVASLEWVSREPALLCTFPNPSAPRKDSTLSAVPQSSYPLLANGVCKWPGC

EKVFEEPEDFLKHCQADHLLDEKGRAQCLLQREMVQSLEQQLVLEKEKLSA

MQAHLAGKMALTKASSVASSDKGSCCIVAAGSQGPVVPAWSGPREAPDSLF

AVRRHLWGSHGNSTFPEFLHNMDYFKFHNMRPPFTYATLIRWAILEAPEKQ

RTLNEIYHWFTRMFAFFRNHPATWKNAIRHNLSLHKCFVRVESEKGAVWTV

DELEFRKKRSQRPSRCSNPTPGP.
```

Suitably, the FOXP3 polypeptide comprises an amino acid sequence set forth in SEQ ID NO: 17, or a fragment thereof. Suitably the FOXP3 polypeptide comprises an amino acid sequence which is at least 80% identical to SEQ ID NO: 17 or a fragment thereof. Suitably, the polypeptide comprises an amino acid sequence which is 85, 90, 95, 98 or 99% identical to SEQ ID NO: 17 or a fragment thereof. Suitably the fragment retains FOXP3 activity. Suitably the fragment is able to bind to FOXP3 targets and act as a transcription factor.

Suitably, the FOXP3 polypeptide may be a natural variant of SEQ ID NO: 17. Suitably, the FOXP3 polypeptide is an isoform of SEQ ID NO: 17. For example, the FOXP3 polypeptide may comprise a deletion of amino acid positions 72-106 relative to SEQ ID NO: 17. Alternatively, the FOXP3 polypeptide may comprise a deletion of amino acid positions 246-272 relative to SEQ ID NO: 17.

Suitably, the FOXP3 polypeptide comprises the amino acid sequence set forth in SEQ ID NO: 25:

```
                                   (SEQ ID NO: 25)
MPNPRPGKPSAPSLALGPSPGASPSWRAAPKASDLLGARGPGGTFQGRDLR

GGAHASSSSLNPMPPSQLQLPTLPLVMVAPSGARLGPLPHLQALLQDRPHF

MHQLSTVDAHARTPVLQVHPLESPAMISLTPPTTATGVFSLKARPGLPPGI

NVASLEWVSREPALLCTFPNPSAPRKDSTLSAVPQSSYPLLANGVCKWPGC

EKVFEEPEDFLKHCQADHLLDEKGRAQCLLQREMVQSLEQVEELSAMQAHL

AGKMALTKASSVASSDKGSCCIVAAGSQGPVVPAWSGPREAPDSLFAVRRH

LWGSHGNSTFPEFLHNMDYFKFHNMRPPFTYATLIRWAILEAPEKQRTLNE

IYHWFTRMFAFFRNHPATWKNAIRHNLSLHKCFVRVESEKGAVWTVDELEF

RKKRSQRPSRCSNPTPGPEGRGSLLTCGDVEEN.
```

Suitably, the FOXP3 polypeptide comprises an amino acid sequence set forth in SEQ ID NO: 25, or a fragment thereof. Suitably the FOXP3 polypeptide comprises an amino acid sequence which is at least 80% identical to SEQ ID NO: 25 or a fragment thereof. Suitably, the polypeptide comprises an amino acid sequence which is 85, 90, 95, 98 or 99% identical to SEQ ID NO: 25 or a fragment thereof. Suitably the fragment retains FOXP3 activity. Suitably the fragment is able to bind to FOXP3 targets and act as a transcription factor.

Suitably, the FOXP3 polypeptide may be a natural variant of SEQ ID NO: 25. Suitably, the FOXP3 polypeptide is an isoform of SEQ ID NO: 25. For example, the FOXP3 polypeptide may comprise a deletion of amino acid positions 72-106 relative to SEQ ID NO: 25. Alternatively, the FOXP3 polypeptide may comprise a deletion of amino acid positions 246-272 relative to SEQ ID NO: 25.

Suitably, the FOXP3 polypeptide is encoded by the polynucleotide sequence set forth in SEQ ID NO: 29:

```
                                   (SEQ ID NO: 27)
ATGCCCAACCCCAGGCCTGGCAAGCCCTCGGCCCCTTCCTTGGCCCTTGGC

CCATCCCCAGGAGCCTCGCCCAGCTGGAGGGCTGCACCCAAAGCCTCAGAC

CTGCTGGGGGCCCGGGGCCCAGGGGGAACCTTCCAGGGCCGAGATCTTCGA

GGCGGGGCCCATGCCTCCTCTTCTTCCTTGAACCCCATGCCACCATCGCAG

CTGCAGCTGCCCACACTGCCCCTAGTCATGGTGGCACCCTCCGGGGCACGG

CTGGGCCCCTTGCCCCACTTACAGGCACTCCTCCAGGACAGGCCACATTTC

ATGCACCAGCTCTCAACGGTGGATGCCCACGCCCGGACCCCTGTGCTGCAG

GTGCACCCCCTGGAGAGCCCAGCCATGATCAGCCTCACACCACCCACCACC

GCCACTGGGGTCTTCTCCCTCAAGGCCCGGCCTGGCCTCCCACCTGGGATC

AACGTGGCCAGCCTGGAATGGGTGTCCAGGGAGCCGGCACTGCTCTGCACC

TTCCCAAATCCCAGTGCACCCAGGAAGGACAGCACCCTTTCGGCTGTGCCC

CAGAGCTCCTACCCACTGCTGGCAAATGGTGTCTGCAAGTGGCCCGGATGT

GAGAAGGTCTTCGAAGAGCCAGAGGACTTCCTCAAGCACTGCCAGGCGGAC

CATCTTCTGGATGAGAAGGGCAGGGCACAATGTCTCCTCCAGAGAGAGATG
```

-continued

```
GTACAGTCTCTGGAGCAGCAGCTGGTGCTGGAGAAGGAGAAGCTGAGTGCC

ATGCAGGCCCACCTGGCTGGGAAAATGGCACTGACCAAGGCTTCATCTGTG

GCATCATCCGACAAGGGCTCCTGCTGCATCGTAGCTGCTGGCAGCCAAGGC

CCTGTCGTCCCAGCCTGGTCTGGCCCCGGGAGGCCCCTGACAGCCTGTTT

GCTGTCCGGAGGCACCTGTGGGGTAGCCATGGAAACAGCACATTCCCAGAG

TTCCTCCACAACATGGACTACTTCAAGTTCCACAACATGCGACCCCCTTTC

ACCTACGCCACGCTCATCCGCTGGGCCATCCTGGAGGCTCCAGAGAAGCAG

CGGACACTCAATGAGATCTACCACTGGTTCACACGCATGTTTGCCTTCTTC

AGAAACCATCCTGCCACCTGGAAGAACGCCATCCGCCACAACCTGAGTCTG

CACAAGTGCTTTGTGCGGGTGGAGAGCGAGAAGGGGGCTGTGTGGACCGTG

GATGAGCTGGAGTTCCGCAAGAAACGGAGCCAGAGGCCCAGCAGGTGTTCC

AACCCTACACCTGGCCCCTGA
```

In some embodiments of the invention, the polynucleotide encoding the FOXP3 polypeptide or variant comprises a polynucleotide sequence which is at least 80% identical to SEQ ID NO: 27 or a functional fragment thereof. Suitably, the polynucleotide encoding the FOXP3 polypeptide or variant comprises a polynucleotide sequence which is at least 85, 90, 95, 98 or 99% identical to SEQ ID NO: 27 or a functional fragment thereof. In some embodiments of the invention, the polynucleotide encoding the FOXP3 polypeptide or variant comprises SEQ ID NO: 27 or a functional fragment thereof.

Suitably, the FOXP3 polypeptide is encoded by the nucleic acid sequence set forth in SEQ ID NO: 24:

```
                                    (SEQ ID NO: 24)
GAATTCGTCGACATGCCCAACCCCAGACCCGGCAAGCCTTCTGCCCCTTCT

CTGGCCCTGGGACCATCTCCTGGCGCCTCCCCATCTTGGAGAGCCGCCCCT

AAAGCCAGCGATCTGCTGGGAGCTAGAGGCCCTGGCGGCACATTCCAGGGC

AGAGATCTGAGAGGCGGAGCCCACGCCTCTAGCAGCAGCCTGAATCCCATG

CCCCCTAGCCAGCTGCAGCTGCCTACACTGCCTCTCGTGATGGTGGCCCCT

AGCGGAGCTAGACTGGGCCCTCTGCCTCATCTGCAGGCTCTGCTGCAGGAC

CGGCCCCACTTTATGCACCAGCTGAGCACCGTGGACGCCCACGCCAGAACA

CCTGTGCTGCAGGTGCACCCCCTGGAAAGCCCTGCCATGATCAGCCTGACC

CCTCCAACCACAGCCACCGGCGTGTTCAGCCTGAAGGCCAGACCTGGACTG

CCCCCTGGCATCAATGTGGCCAGCCTGGAATGGGTGTCCCGCGAACCTGCC

CTGCTGTGCACCTTCCCCAATCCTAGCGCCCCCAGAAAGGACAGCACACTG

TCTGCCGTGCCCCAGAGCAGCTATCCCCTGCTGGCTAACGGCGTGTGCAAG

TGGCCTGGCTGCGAGAAGGTGTTCGAGGAACCCGAGGACTTCCTGAAGCAC

TGCCAGGCCGACCATCTGCTGGACGAGAAAGGCAGAGCCCAGTGCCTGCTG

CAGCGCGAGATGGTGCAGTCCCTGGAACAGCAGCTGGTGCTGGAAAAAGAA

AAGCTGAGCGCCATGCAGGCCCACCTGGCCGGAAAGATGGCCCTGACAAAA

GCCAGCAGCGTGGCCAGCTCCGACAAGGGCAGCTGTTGTATCGTGGCCGCT

GGCAGCCAGGGACCTGTGGTGCCTGCTTGGAGCGGACCTAGAGAGGCCCCC

GATAGCCTGTTTGCCGTGCGGAGACACCTGTGGGGCAGCCACGGCAACTCT

ACCTTCCCCGAGTTCCTGCACAACATGGACTACTTCAAGTTCCACAACATG

AGGCCCCCCTTCACCTACGCCACCCTGATCAGATGGGCCATTCTGGAAGCC

CCCGAGAAGCAGCGGACCCTGAACGAGATCTACCACTGGTTTACCCGGATG

TTCGCCTTCTTCCGGAACCACCCCGCCACCTGGAAGAACGCCATCCGGCAC

AATCTGAGCCTGCACAAGTGCTTCGTGCGGGTGGAAAGCGAGAAGGGCGCC

GTGTGGACAGTGGACGAGCTGGAATTTCGGAAGAAGCGGTCCCAGAGGCCC

AGCCGGTGTAGCAATCCTACACCTGGCCCTGAGGGCAGAGGAAGTCTGCTA

ACATGCGGTGACGTCGAGGAGAATCC.
```

Suitably, the FOXP3 polypeptide is encoded by the nucleic acid sequence set forth in SEQ ID NO: 24, or a fragment thereof. Suitably the FOXP3 polypeptide is encoded by a nucleic acid sequence which is at least 80% identical to SEQ ID NO: 24 or a fragment thereof. Suitably, the FOXP3 polypeptide is encoded by the nucleic acid sequence which is 85, 90, 95, 98 or 99% identical to SEQ ID NO: 24 or a fragment thereof. Suitably the fragment retains FOXP3 activity. Suitably the polypeptide encoded by the fragment is able to bind to FOXP3 targets and act as a transcription factor.

The term "vector" includes an expression vector, i.e., a construct enabling expression of TCR i.e. an α chain and/or β chain according to the present invention. Suitably the expression vector additionally enables expression of a FOXP3 polypeptide. In some embodiments, the vector is a cloning vector.

Suitable vectors may include, but are not limited to, plasmids, viral vectors, transposons, nucleic acid complexed with polypeptide or immobilised onto a solid phase particle.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763) incorporated herein by reference.

Lentiviruses also belong to the retrovirus family, but they can infect both dividing and non-dividing cells (Lewis et al (1992) EMBO J. 3053-3058) incorporated herein by reference.

The vector may be capable of transferring a polynucleotide the invention to a cell, for example a host cell as defined herein. The vector should ideally be capable of sustained high-level expression in host cells, so that the α chain and/or β chain are suitably expressed in the host cell.

The vector may be a retroviral vector. The vector may be based on or derivable from the MP71 vector backbone. The vector may lack a full-length or truncated version of the Woodchuck Hepatitis Response Element (WPRE).

For efficient infection of human cells, viral particles may be packaged with amphotropic envelopes or gibbon ape leukemia virus envelopes.

Cell

The present invention further provides a cell e.g. a host cell comprising a polynucleotide or vector according to the invention.

The host cell may be any cell which can be used to express and produce a TCR.

Suitably, the cell is a T cell, such as a conventional T cell.
Suitably, the cell is a Treg cell.

In one aspect, the cell, such as a T cell or Treg, may be isolated from blood obtained from the subject. Suitably, the cell, such as a T cell or Treg, is isolated from peripheral blood mononuclear cells (PBMCs) obtained from the subject.

Suitably, the cell is a natural T reg which expresses FOXP3.

In one aspect, the cell is a stem cell.
In another aspect, the cell is a progenitor cell.

As used herein, the term "stem cell" means an undifferentiated cell which is capable of indefinitely giving rise to more stem cells of the same type, and from which other, specialised cells may arise by differentiation. Stem cells are multipotent. Stem cells may be for example, embryonic stem cells or adult stem cells.

As used herein, the term "progenitor cell" means a cell which is able to differentiate to form one or more types of cells but has limited self-renewal in vitro.

Suitably, the cell is capable of being differentiated into a T cell, such as a Treg.

Suitably, the cell has the ability to differentiate into a T cell, which expresses FOXP3 such as a Treg.

Suitably, the cell is a human cell. Suitable the cell is a human Treg.

Suitably, the cell may be an embryonic stem cell (ESC). Suitably, the cell is a haematopoietic stem cell or haematopoietic progenitor cell. Suitably, the cell is an induced pluripotent stem cell (iPSC). Suitably, the cell may be obtained from umbilical cord blood. Suitably, the cell may be obtained from adult peripheral blood.

In some aspects, hematopoietic stem and progenitor cell (HSPCs) may be obtained from umbilical cord blood. Cord blood can be harvested according to techniques known in the art (e.g., U.S. Pat. Nos. 7,147,626 and 7,131,958 which are incorporated herein by reference).

In one aspect, HSPCs may be obtained from pluripotent stem cell sources, e.g., induced pluripotent stem cells (iPSCs) and embryonic stem cells (ESCs).

As used herein, the term "hematopoietic stem and progenitor cell" or "HSPC" refers to a cell which expresses the antigenic marker CD34 (CD34+) and populations of such cells. In particular embodiments, the term "HSPC" refers to a cell identified by the presence of the antigenic marker CD34 (CD34+) and the absence of lineage (lin) markers. The population of cells comprising CD34+ and/or Lin(−) cells includes haematopoietic stem cells and hematopoietic progenitor cells.

HSPCs can be obtained or isolated from bone marrow of adults, which includes femurs, hip, ribs, sternum, and other bones. Bone marrow aspirates containing HSPCs can be obtained or isolated directly from the hip using a needle and syringe. Other sources of HSPCs include umbilical cord blood, placental blood, mobilized peripheral blood, Wharton's jelly, placenta, fetal blood, fetal liver, or fetal spleen. In particular embodiments, harvesting a sufficient quantity of HSPCs for use in therapeutic applications may require mobilizing the stem and progenitor cells in the subject.

As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell (HSC and HPC respectively).

As used herein, the term "reprogramming" refers to a method of increasing the potency of a cell to a less differentiated state.

As used herein, the term "programming" refers to a method of decreasing the potency of a cell or differentiating the cell to a more differentiated state.

Suitably the cell is matched or is autologous to the subject. The cell may be generated ex vivo either from a patient's own peripheral blood (1st party), or in the setting of a haematopoietic stem cell transplant from donor peripheral blood (2nd party), or peripheral blood from an unconnected donor (3rd party).

Suitably the cell is autologous to the subject. Suitably, the subject is a human.

In some aspects, the cell may be derived from ex-vivo differentiation of inducible progenitor cells or embryonic progenitor cells to the immune cell. In these instances, cells are generated by introducing DNA or RNA coding for the TCR of the present invention by one of many means including transduction with a viral vector, transfection with DNA or RNA.

Suitably, the cells are generated by introducing in addition to the TCR of the invention, DNA or RNA coding for FOXP3 by one of many means including transduction with a viral vector, or transfection with DNA or RNA.

As used herein, the term "conventional T cell" or Tconv means a T lymphocyte cell which expresses an αβ T cell receptor (TCR) as well as a co-receptor which may be cluster of differentiation 4) CD4 or cluster of differentiation 8 (CD8). Conventional T cells are present in the peripheral blood, lymph nodes, and tissues. FOXP3 is expressed by thymus derived Tregs and can be expressed by recently activated conventional T cells.

As used herein, the term "regulatory T cell" or Treg, means a T cell which expresses the markers CD4, CD25 and FOXP3 ($CD4^+CD25^+FOXP3^+$). Tregs may also be identified using the cell surface markers CD4 and CD25 in the absence of or in combination with low-level expression of the surface protein CD127 ($CD4^+CD25^+CD127^-$). Tregs may also express on the cell surface, high levels of CTLA-4 (cytotoxic T-lymphocyte associated molecule-4) or GITR (glucocorticoid-induced TNF receptor). Unlike conventional T cells, regulatory T cells do not produce IL-2 and are therefore anergic at baseline. Treg cells include thymus-derived, natural Treg (nTreg) cells and peripherally generated, induced Treg (iTreg) cells.

In one aspect, a Treg is $CD4^+CD25^+FOXP3^+$. T cell.
In one aspect, a Treg is a $CD4^+CD25^+CD127^-$ T cell.
In one aspect, a Treg is a $CD4^+CD25^+FOXP3^+CD127^-$ T cell.

As used herein, the term "natural T reg" means a thymus-derived Treg. Natural T regs are CD4$^+$CD25$^+$FOXP3$^+$ Helios$^+$ Neuropilin 1$^+$. Compared with iTregs, nTregs have higher expression of PD-1 (programmed cell death-1, pdcd1), neuropilin 1 (Nrp1), Helios (Ikzf2), and CD73. nTregs may be distinguished from iTregs on the basis of the expression of Helios protein or Neuropilin 1 (Nrp1) individually.

As used herein, the term "induced regulatory T cell" (iTreg) means a CD4$^+$ CD25$^+$ FOXP3$^+$ Helios$^-$ Neuropilin 1$^-$ T cell which develops from mature CD4+ conventional T cells outside of the thymus. For example, iTregs can be induced in vitro from CD4+ CD25−FOXP3− cells in the presence of IL-2 and TGF-β.

Compositions

The present invention also provides a composition comprising an engineered Treg, a vector or a cell according to the invention. Suitably the present invention provides a composition comprising an engineered Treg according to the invention. Suitably the present invention provides a composition comprising a vector according to the invention. Suitably the present invention provides a composition comprising a cell according to the invention.

In some embodiments, the composition is a pharmaceutical composition. Such pharmaceutical composition may comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s) and other carrier agents.

The pharmaceutical compositions typically should be sterile and stable under the conditions of manufacture and storage. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent. A pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers which are non-toxic to the subjects at the dosages and concentrations employed. Preferably, such a composition can further comprise a pharmaceutically acceptable carrier or excipient for use in the treatment of disease that that is compatible with a given method and/or site of administration, for instance for parenteral (e.g. sub-cutaneous, intradermal, or intravenous injection) or intrathecal administration.

Wherein the pharmaceutical composition comprises a cell according to the invention, the composition may be produced using current good manufacturing practices (cGMP).

Suitably the pharmaceutical composition comprising a cell may comprise an organic solvent, such as but not limited to, methyl acetate, dimethyl sulfoxide (DMSO), N,N-dimethylformamide (DMF), dimethoxyethane (DME), and dimethylacetamide, including mixtures or combinations thereof.

Suitably the pharmaceutical composition comprising a cell is endotoxin free.

Method of Treatment

The present invention provides a method for treating and/or preventing a disease which comprises the step of administering an engineered Treg of the present invention to a subject.

The present invention provides a method for treating and/or preventing a disease which comprises the step of administering a pharmaceutical composition of the present invention to a subject.

The present invention also provides an engineered Treg of the present invention for use in treating and/or preventing a disease.

The present invention also provides a pharmaceutical composition of the present invention for use in treating and/or preventing a disease.

The invention also relates to the use of an engineered Treg, a vector or cell according to the present invention in the manufacture of a medicament for treating and/or preventing a disease.

Preferably, the present methods of treatment relate to the administration of a pharmaceutical composition of the present invention to a subject.

The term "treat/treatment/treating" refers to administering an engineered Treg, cell, vector, or pharmaceutical composition as described herein to a subject having an existing disease or condition in order to lessen, reduce or improve at least one symptom associated with the disease and/or to slow down, reduce or block the progression of the disease.

Reference to "prevention"/"preventing" (or prophylaxis) as used herein refers to delaying or preventing the onset of the symptoms of the disease. Prevention may be absolute (such that no disease occurs) or may be effective only in some individuals or for a limited amount of time.

In a preferred embodiment of the present invention, the subject of any of the methods described herein is a mammal, preferably a cat, dog, horse, donkey, sheep, pig, goat, cow, mouse, rat, rabbit or guinea pig. Preferably the subject is a human.

The administration of a pharmaceutical composition of the invention can be accomplished using any of a variety of routes that make the active ingredient bioavailable. For example, a Treg, cell, vector, or pharmaceutical composition can be administered intravenously, intrathecally, by oral and parenteral routes, intranasally, intraperitoneally, subcutaneously, transcutaneously or intramuscularly.

In one aspect, the engineered Treg according to the invention or the pharmaceutical composition according to the invention is administered intravenously.

In another aspect, the engineered Treg according to the invention or the pharmaceutical composition according to the invention is administered intrathecally.

Typically, a physician will determine the actual dosage that is most suitable for an individual subject and it will vary with the age, weight and response of the particular patient. The dosage is such that it is sufficient to reduce and/or prevent disease symptoms.

Those skilled in the art will appreciate, for example, that route of delivery (e.g., oral vs intravenous vs subcutaneous, etc) may impact dose amount and/or required dose amount may impact route of delivery. For example, where particularly high concentrations of an agent within a particular site or location are of interest, focused delivery may be desired and/or useful. Other factors to be considered when optimizing routes and/or dosing schedule for a given therapeutic regimen may include, for example, the disease being treated (e.g., type or stage, etc.), the clinical condition of a subject (e.g., age, overall health, etc.), the presence or absence of combination therapy, and other factors known to medical practitioners.

The dosage is such that it is sufficient to stabilise or improve symptoms of the disease.

The present invention also provides a method for treating and/or preventing a disease, which comprises the step of administering a pharmaceutical composition comprising a cell e.g. a T cell according to the invention to a subject.

Suitably, the present invention also provides a method for treating and/or preventing a disease, which comprises the step of administering an engineered Treg according to the invention to a subject.

The method may comprise the following steps:
(i) isolation of a cell-containing sample from a subject;
(ii) introducing a nucleic acid sequence encoding a TCR and optionally, a nucleic acid encoding a FOXP3 protein to the cells; and
(iii) administering the cells from (ii) to the subject.

Suitably the cells from (ii) may be expanded in vitro before administration to the subject.

Disease

The disease to be treated and/or prevented by the methods and uses of the present invention may be any disease which induces a T cell mediated immune response.

The disease may be, for example, a cancer, infectious disease or autoimmune disease.

Suitably the disease to be treated and/or prevented by the methods and uses of the present invention may be an autoimmune disease.

Without wishing to be bound by theory, the disease to be treated and/or prevented by the methods and uses of the present invention may be any disease wherein MBP is an antigen e.g.
where MBP is a self-antigen.

Suitably the disease may be an autoimmune and inflammatory central nervous system disease (e.g. chronic neurodegenerative conditions).

Suitably the disease may be a chronic neurodegenerative condition such as multiple sclerosis (MS), Alzheimer's disease, Parkinson's disease, neurotropic viral infections, stroke, paraneoplastic disorders and traumatic brain injury.

In one aspect, the disease is multiple sclerosis.

Suitably, the disease is chronic progressive multiple sclerosis.

Suitably, the disease is relapsing/remitting multiple sclerosis.

In one aspect, the disease may have central nervous system (CNS) involvement of systemic autoimmune and inflammatory disease such as Behçet disease, sarcoidosis, systemic lupus erythematosus, juvenile idiopathic arthritis, scleroderma, and Sjögren syndrome.

Suitably, the disease is present in an HLA-DRB1*0401 positive subject.

Suitably, the disease is multiple sclerosis and the subject is HLA-DRB1*0401 positive.

Suitably, the disease is chronic progressive multiple sclerosis and the subject is HLA-DRB1*0401 positive.

Suitably, the disease is relapsing/remitting multiple sclerosis and the subject is HLA-DRB1*0401 positive.

Multiple Sclerosis

Multiple Sclerosis (MS) is the most common neurological disorder among young adults in Europe and in the USA. MS is characterised as a demyelinating disease and is a chronic degenerative disease of the central nervous system in which gradual destruction of myelin occurs in patches throughout the brain and/or spinal cord, interfering with neural connectivity and causing muscular weakness, loss of coordination and speech and visual disturbances.

Several types or patterns of progression of MS have been identified including, clinically isolated syndrome (CIS), relapsing-remitting MS (RRMS), primary progressive MS (PPMS) and secondary progressive MS (SPMS). For some patients, the increase or progression of disability is very gradual, and for others it can occur more quickly. In general, however, recovery from attacks become less and less complete, and symptoms tend to increase and disability grows.

Although several disease-modifying treatments (DMTs) have been approved to reduce the frequency of clinical relapses, most patients continue to clinically deteriorate under current therapy schedules. Autologous haematopoietic stem cell transplantation can have lasting beneficial effects for patients, but the procedure requires aggressive myeloablative conditioning which is associated with substantial toxicity. Neither DMTs nor stem cell transplantation can mediate antigen-specific suppression of the immunopathology of MS. Without wishing to be bound by theory, in the future, administration of one dose of engineered Treg of the present invention may provide lasting suppression of MS immunopathology in the absence of systemic side effects. This will have a significant impact on the progression of the disease in people with MS.

Suitably, the Treg, vector or pharmaceutical composition of the present invention may reduce or ameliorate one or more of the symptoms of MS, which include reduced or loss of vision, stumbling and uneven gait, slurred speech, urinary frequency and incontinence, mood changes and depression, muscle spasms and paralysis.

Method

The invention also provides a method for producing an engineered Treg which method comprises introducing into a cell in vitro or ex vivo, a polynucleotide encoding a TCR as defined herein. Suitably, the method further comprises incubating the cell under conditions permitting expression of the TCR molecule of the present invention. Optionally, the method may further comprise a step of purifying the engineered Treg cells.

Suitably, the cell is a T cell.
Suitably, the cell is a Treg cell.
Suitably, the cell is a natural Treg which expresses FOXP3.

In one aspect, the cell is a stem cell. Suitably, in the method according to the invention, a nucleic acid encoding TCR as defined herein has been introduced into the stem cell and the stem cell is then differentiated into a T cell such as a Treg which expresses FOXP3.

Suitably, the stem cell has the ability to differentiate into a T cell such as a Treg which expresses FOXP3. Suitably, the cell may be an embryonic stem cell (ESC). Suitably, the cell may be obtained from umbilical cord blood. Suitably, the cell may be obtained from adult peripheral blood. Suitably, the cell is a haematopoietic stem and progenitor cell (HSPC). Suitably, the cell is an induced pluripotent stem cell (iPSC).

In another aspect, the cell is a progenitor cell. Suitably the progenitor cell has the ability to differentiate into a T cell such as a Treg which expresses FOXP3.

In another aspect, the invention provides a method for producing an engineered Treg, which method comprises introducing into a cell in vitro or ex vivo a polynucleotide encoding a TCR as defined herein and a polynucleotide encoding a FOXP3 protein. Suitably the polynucleotide encoding a TCR as defined herein and the polynucleotide encoding a FOXP3 protein are provided as separate polynucleotides. Suitably the separate polypeptides are introduced separately, sequentially or simultaneously into the cell. Wherein the polypeptides are introduced separately or sequentially, suitably the polynucleotide encoding the TCR is introduced first. Wherein the polypeptides are introduced separately or sequentially, suitably the polynucleotide encoding FOXP3 is introduced first. Suitably the polynucleotide encoding a TCR as defined herein and the polynucleotide encoding a FOXP3 protein are provided on the same polynucleotide.

Suitably, the method further comprises incubating the cell under conditions causing expression of FOXP3 and the TCR molecule of the present invention. Optionally, the method may further comprise a step of purifying the engineered Treg cells.

In one aspect, the invention provides a method for producing an engineered Treg, which method comprises introducing into a cell in vitro or ex vivo a polynucleotide encoding a TCR as defined herein and a polynucleotide encoding a FOXP3 protein and differentiating the cell into a T cell, such as a Treg which expresses FOXP3. Suitably, the method further comprises incubating the cell under conditions causing expression of FOXP3 and the TCR molecule of the present invention. Optionally, the method may further comprise a step of purifying the engineered Treg cells.

Suitably, in one aspect the cell is differentiated into a T cell before FOXP3 is introduced into the cell.

Purification of the engineered Treg may be achieved by any method known in the art. Suitably, the engineered Treg may be purified using fluorescence-activated cell sorting (FACS) or immunomagnetic isolation (i.e. using antibodies attached to magnetic nanoparticles or beads) using positive and/or negative selection of cell populations.

Suitably, purification of the engineered T cell may be performed using the expression of the TCR as defined herein.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

It is noted that embodiments of the invention as described herein may be combined.

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1—Production of Retroviral Vectors Encoding TCR and TCR+FOXP3

MS2-3C8 TCR

Figure 1:
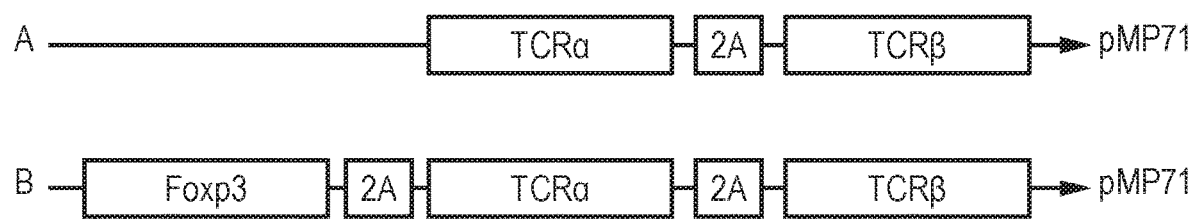
FIG. 1—shows a schematic diagram of a pMP71 retroviral vector encoding (A) MBP TCR alpha and beta chains and (B) FOXP3 plus TCR alpha and beta chains.
Figure 2:
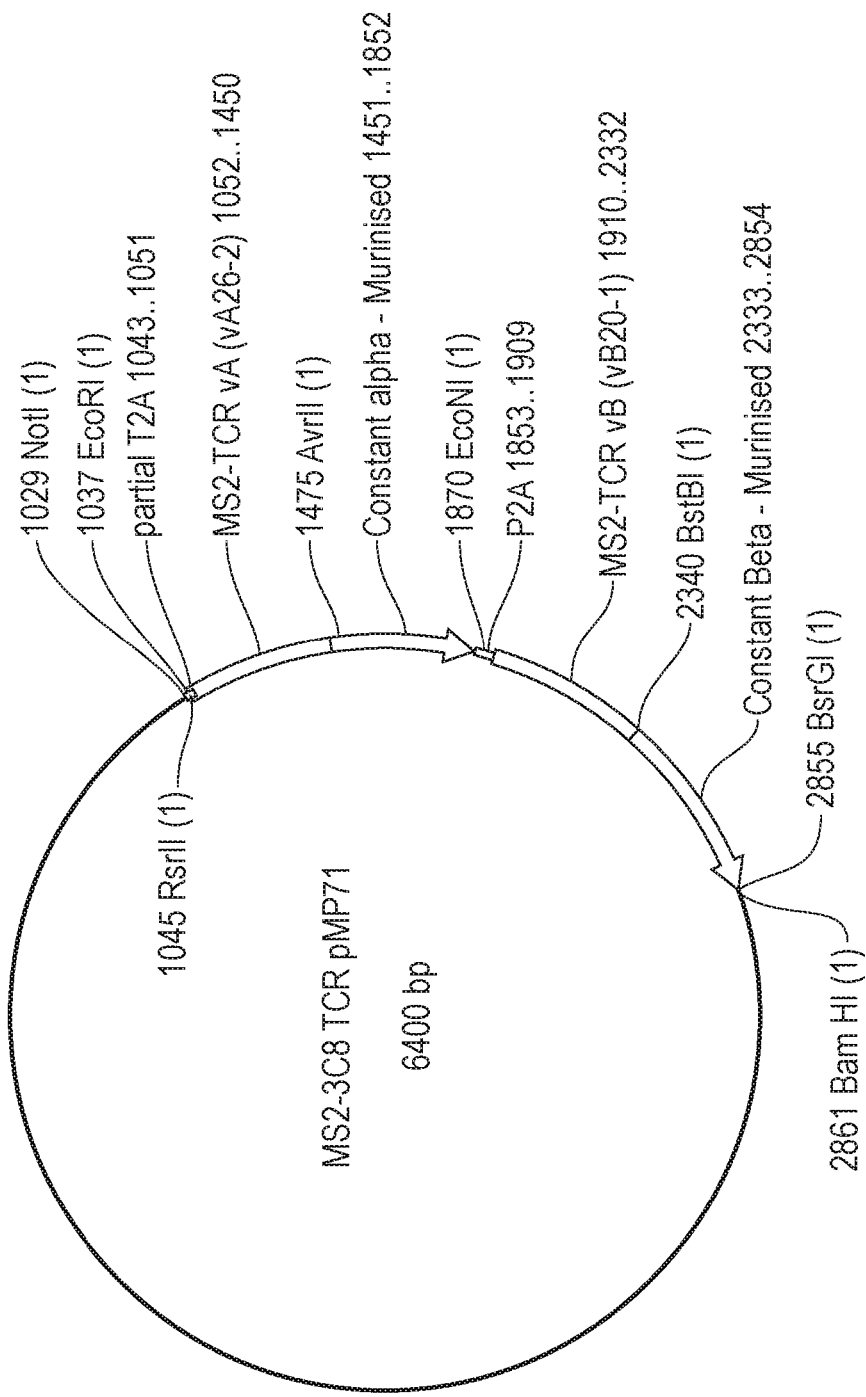
FIG. 2—MS2-3C8 TCR pMP71. MS2-3C8 TCR recognises MBP 111-129 (SEQ ID NO: 3) presented by HLA-DRB1*0401. The TCR has been codon optimised and both constant alpha and beta domains have been murinised, and an extra disulphide bond has been added between c-alpha and c-beta.

The MS2-3C8 TCR recognises MBP 111-129 (SEQ ID NO: 3) presented by HLA-DRB1*0401 as described by Muraro et al., JCI 1997; 100, 2, 339-349, incorporated herein by reference. A codon optimised MS-2 TCR expression cassette coding for the MS2-3C8 TCR was constructed (FIG. 1 and FIG. 2) by cloning the codon optimised MS2-TCR vα, murinised constant alpha domain, codon optimised MS2-TCR vβ and murinised constant beta domain into a retroviral expression cassette, pMP71. An extra disulphide bond was added between the constant-alpha and constant-beta domains as described in Blood. 2007 Mar. 15; 109(6): 2331-2338. and Cancer Res. 2007 Apr. 15; 67(8): 3898-3903, incorporated herein by reference. The constant-alpha and MS2-TCR vβ domains were separated by a P2A sequence.

MS2-3C8 FOXP3

Figure 3:
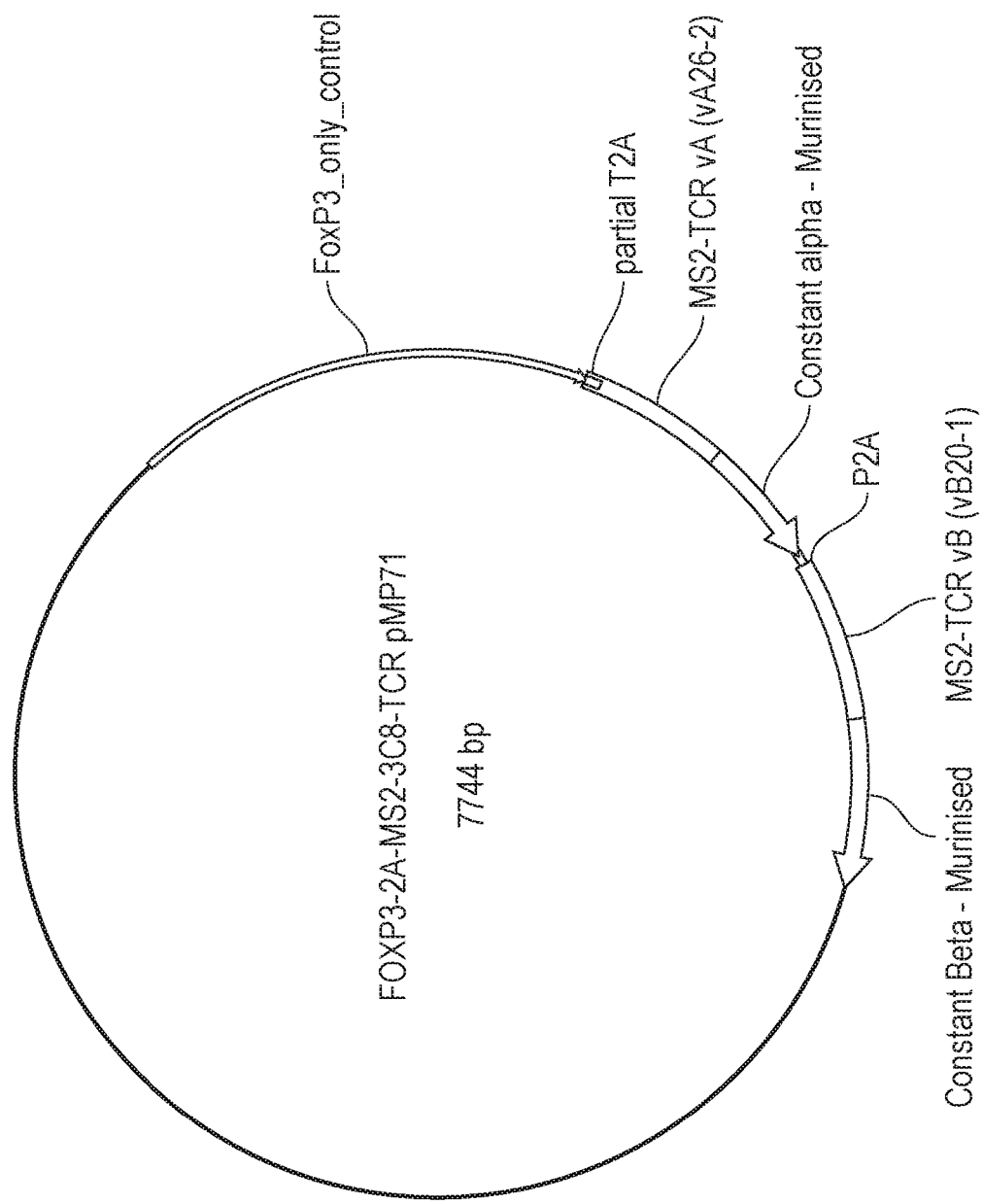
FIG. 3—FOXP3– 2A-MS2-3C8 TCR pMP71 comprising a FOXP3 gene with STOP codon removed at the 3' T2A site, inserted into the RsrII and EcoR1 sites upstream of the MS-2 TCR.
Figure 4:
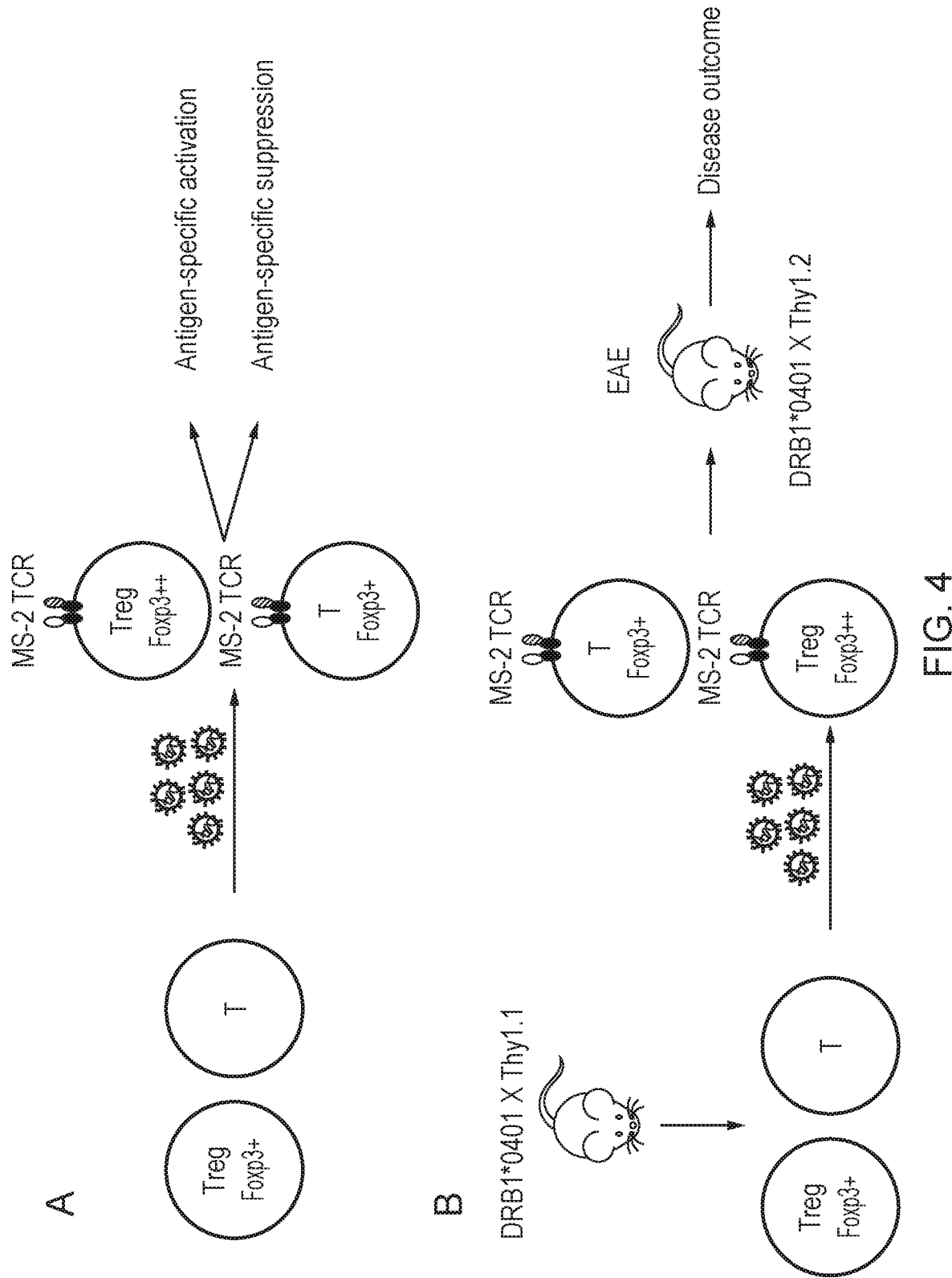
FIG. 4—Schematic showing study design. A) Demonstration of MBP specific suppressive function in an engineered Treg. B) The use of an engineered Treg to suppress MS-like immunopathology in a HLA-transgenic mouse model FIG. 5—Plots show representative flow cytometric analysis performed at day 7 to assess level of transduction through expression of murine TCR constant regions and FOXP3. Treg and Tconv cells are mock transduced, or are transduced with TCR (MS-2) or TCR+FOXP3 (MS-2 FOXP3).

An expression cassette encoding FOXP3 and MS-2 TCR was constructed by modifying the MS-2 TCR described above (FIG. 1 and FIG. 3). A FOXP3 gene with the STOP codon removed and a T2A sequence were inserted into the pMP71 vector using the RsrII and EcoR1 sites upstream of the MS-2 TCR.

Example 2—Transduction of T Cells with TCR and TCR+FOXP3

Phoenix-Ampho cells were seeded at $2 \times 10^6$ in 8 mL of Iscove's Modified Dulbecco's Media (IMDM) in standard tissue culture conditions for 24 hours. On day 1 cells were transfected using FuGENE® transfection reagent and optimum media mixed with 2.5 µg of relevant plasmid DNA and 1.5 µg of pCL-Amp, encoding the ecotropic retroviral co-receptor, for 20 minutes at room temperature. The transfection mixture was added to adherent Phoenix Amphotropic (Phoenix-AMPHO) cells and incubated for a further 24 hours. On day 2 media was changed for 5 mL of Tex-MACS® (Miltenyi) tissue culture media and cells were incubated for a further 24 hours.

CD4+ T cells were isolated using a CD4+ Positive selection kit. Cells were subsequently stained with flow cytometry antibodies CD4, CD25 and CD127 before cell sorting using the BD FACSAria® cytometer.

CD4+CD25hiCD127− Treg and CD4+CD25−CD127+ Tconv were collected in polypropylene tubes. The purity of cell sorting was determined by addition of FOXP3 PE antibody. Purity of CD4+CD25+CD127-FOXP3+ cells was routinely >70%.

On day 0 FACS sorted cells were activated for 48 hours by culturing 1:1 with anti-CD3 and anti-CD28 beads. On day 2 cells were counted and resuspended in complete Roswell Park Memorial Institute medium (RPMI-1640) (Gibco) for Tconv or TexMACS® media for Treg at $1\times10^6$/mL. Non-tissue culture-treated 24-well plates were pre-prepared by coating with retronectin, then subsequently blocked with 2% bovine serum albumin in phosphate buffered saline (PBS) and washed ×2 with PBS. The cell suspension was mixed 1:1. The final concentration of IL-2 was 300 u/ml for Tconv and 1000 u/ml for Treg. Cells were incubated overnight at 37 degrees before removing supernatant and supplementing with fresh complete media and IL-2. The media was changed on alternate days.

Tconv cells were grown in RPMI-1640 supplemented with 10% heat inactivated foetal bovine serum (FBS); 100 Units/mL penicillin; 100 µg/mL streptomycin; 2 mM L-glutamine. Regulatory T cells were cultured in TexMACX® media supplemented with 100 Units/mL penicillin; 100 µg/mL streptomycin.

Figure 5:
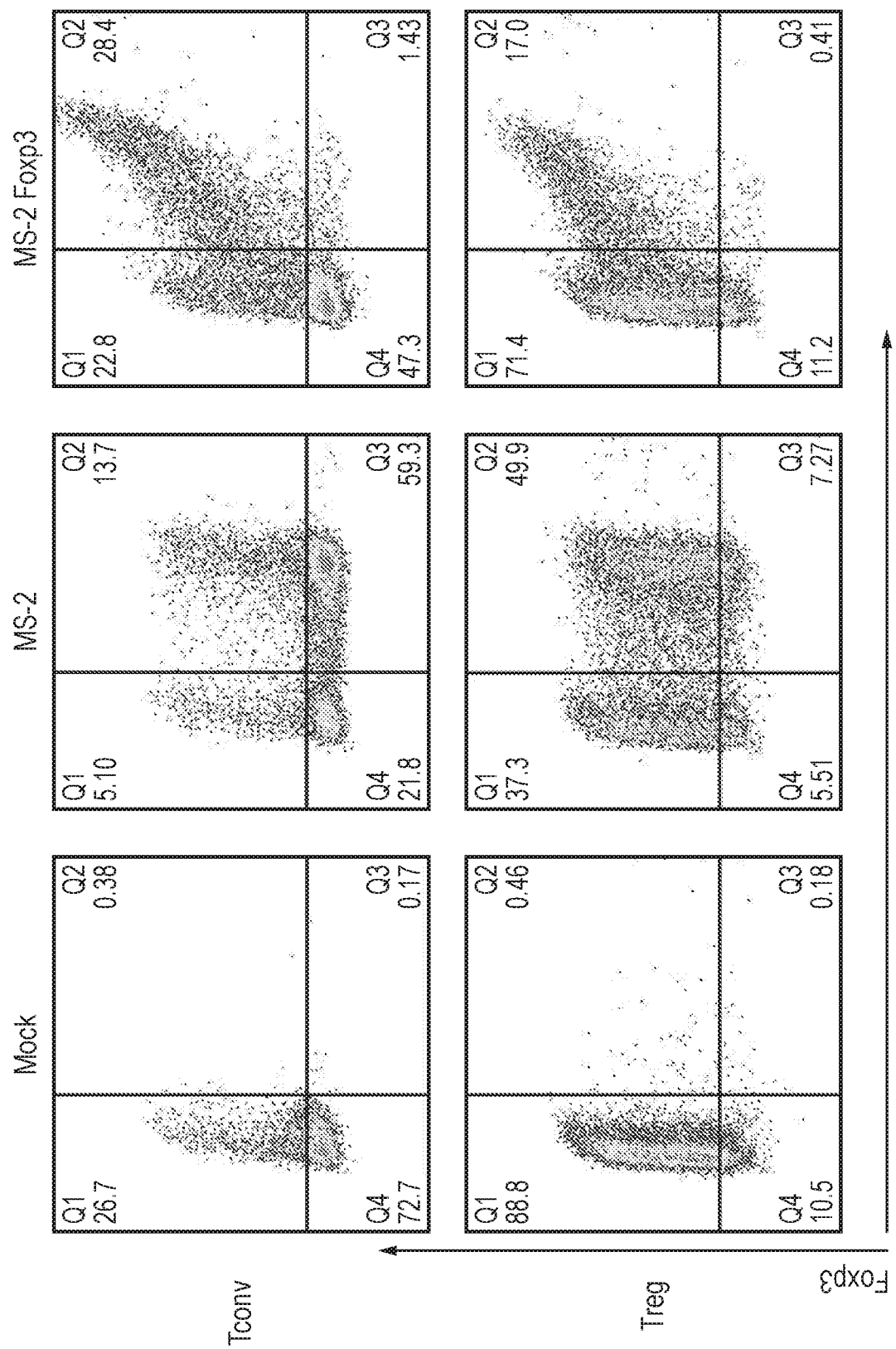

The FACS dot-plots in FIG. 5 show representative flow cytometric analysis performed at day 7 to assess the level of transduction through measurement of the expression of murine TCR constant regions and FOXP3.

Example 3—FOXP3 Expression During In Vitro Expansion

T cells were isolated as described above in Example 2. At day 0 the expression of FOXP3 and Treg cell surface markers CTLA-4 (also known as CD152) and CD25 was measured by flow cytometry.

Figure 6:
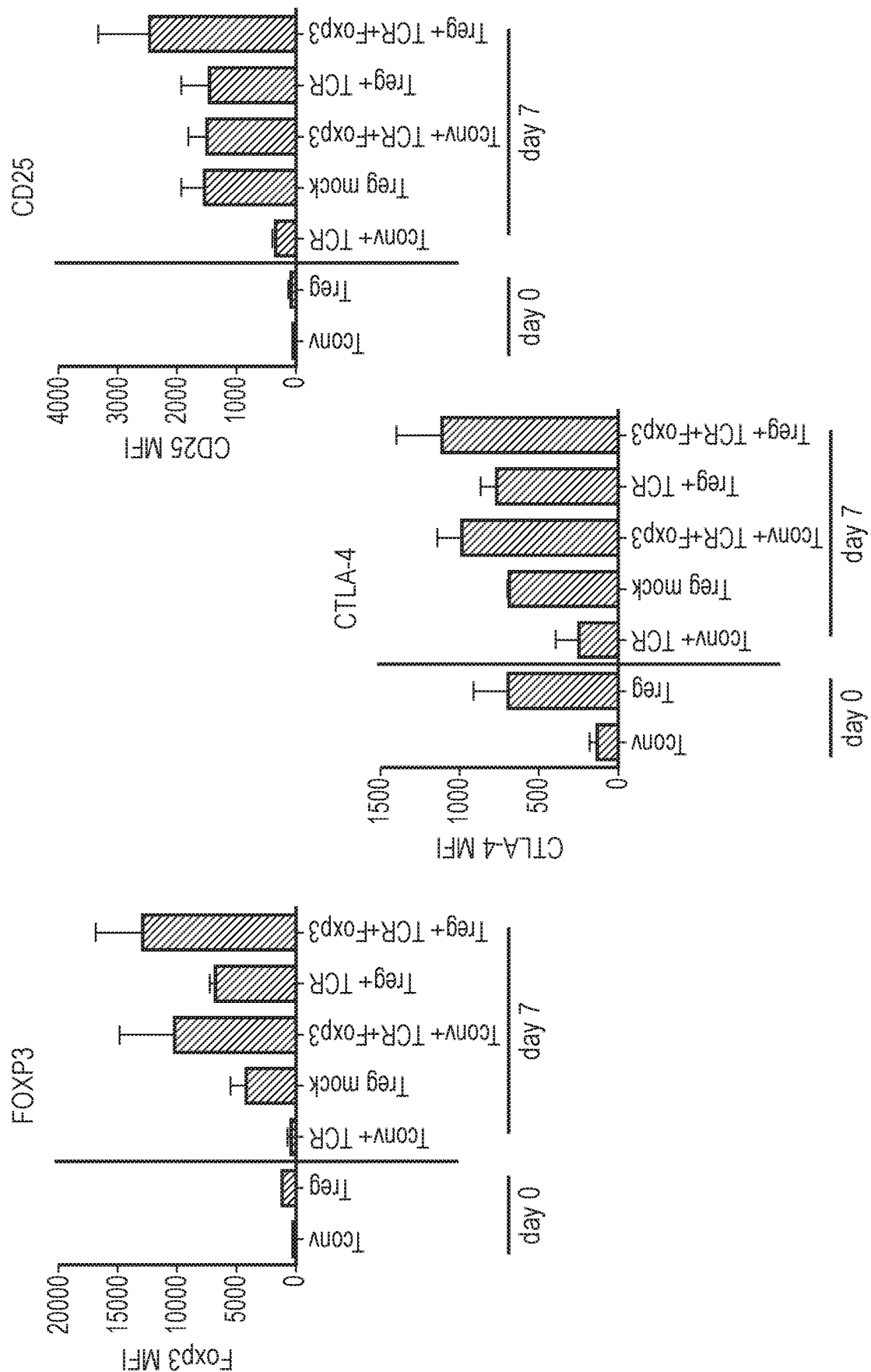
FIG. 6—Graphs showing the relative expression of Treg surface markers on non transduced cells (d0) or gated on transduced cell populations (d7) n=2-4. These results demonstrate that regulatory T cells maintain FOXP3 expression during in vitro expansion.

T cells were transduced and cultured as described above in Example 2. At day 7 the cells were analysed by flow cytometry and the dot-plots were gated on transduced cell populations. The relative expression of FOXP3, CTLA-4 and CD25 was measured. FIG. 6 shows bar charts depicting expression of FOXP3, CTLA-4 and CD25 at day 7 of in vitro expansion. FOXP3 expression is maintained during in vitro expansion.

Antigen-Specific Activation of MS-2 TCR Transduced T Cells

Example 4—Peptide Restimulation of Effector T Cells and Tregs

Chinese Hamster Ovary (CHO) cells were transduced with human HLA-DR4 and CD80 or CD86. Cells expressing CD80 or CD86 were mixed together in equal parts for subsequent experiments.

CHO cells were resuspended at $10\times10^6$/mL in culture media with saturating amounts (10pM/ml) of MBP 111-129 (SEQ ID NO: 3) (LSRFSWGAEGQRPGFGYGG). Suspensions were incubated for 2 hours at standard tissue culture conditions before being irradiated, washed and resuspended.

T cells transduced with MS2 or MS2-FOXP3 construct were washed, counted and resuspended at $0.5\times10^6$ cells/ml in complete RPMI. Cells were plated 1:1 with CHO cells incubated with or without peptide for 4 hours. Cells were fixed and permeablised before staining with antibodies for IL-2 and IFNγ.

Figure 7:
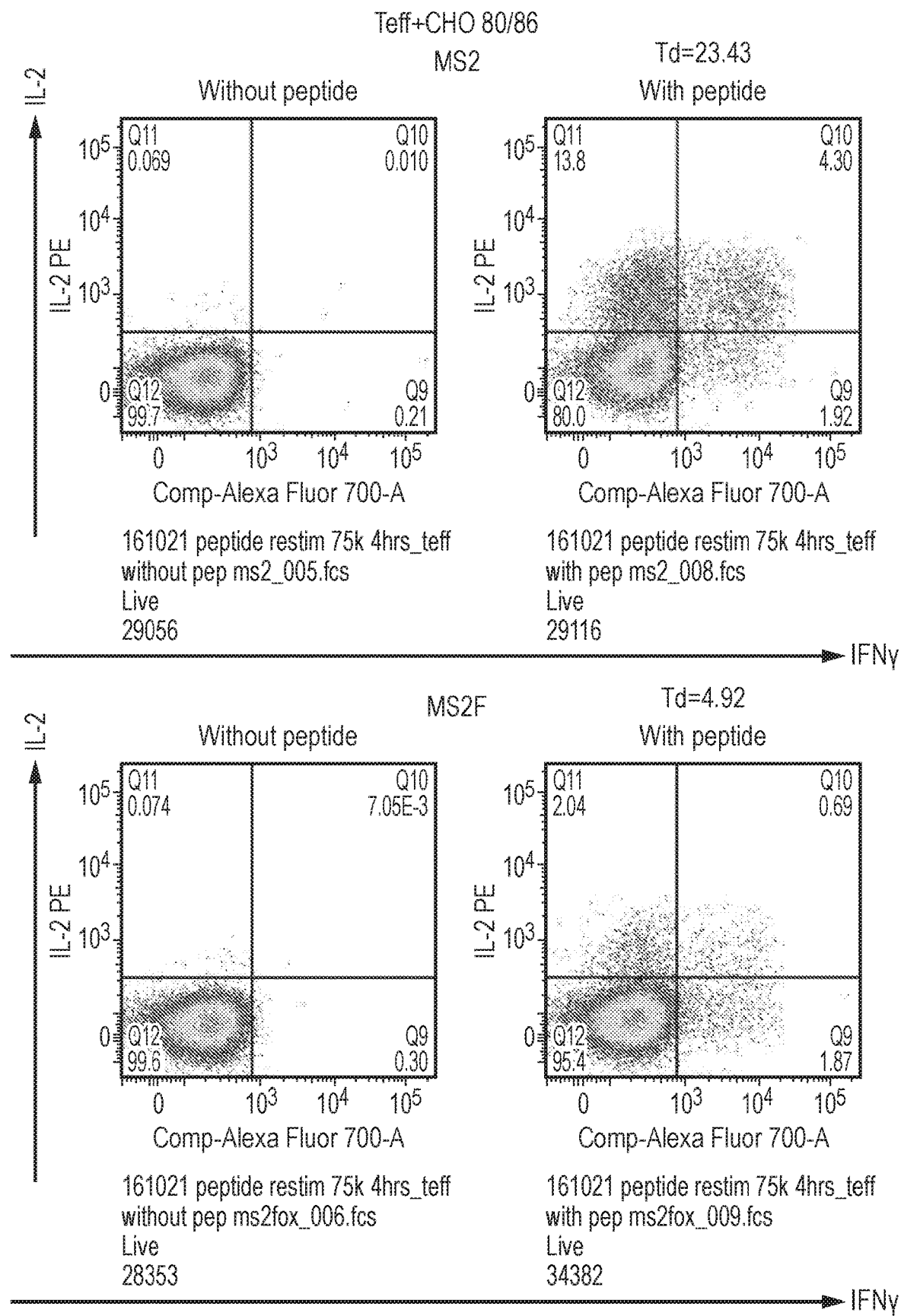
FIG. 7—Graphs showing restimulation of effector T cells with peptide. Chinese Hamster Ovary (CHO) cells were transduced with human HLA-DR4 and CD80 or CD86. Cells expressing CD80 or CD86 were mixed together in equal parts for subsequent experiments. CHO cells were resuspended at $10 \times 10^6$/mL in culture media with saturating amounts (10 ρM/ml) of MBP 111-129 (SEQ ID NO: 3) (LSRFSWGAEGQRPGFGYGG). T cells transduced with a MS2 or MS2-FOXP3 construct were washed, counted and resuspended at $0.5 \times 10^6$ cells/ml in complete RPMI. Cells were plated 1:1 with CHO cells incubated with or without peptide for 4 hours. Cells were fixed and permeablised before staining with antibodies for IL-2 and IFNγ. Transduction efficiency of T cells is indicated by 'Td='.

FIG. 7 demonstrates FACS dot-plots showing peptide restimulation of effector T cells. The transduction efficiency of T cells is indicated by 'Td='.

Figure 8:
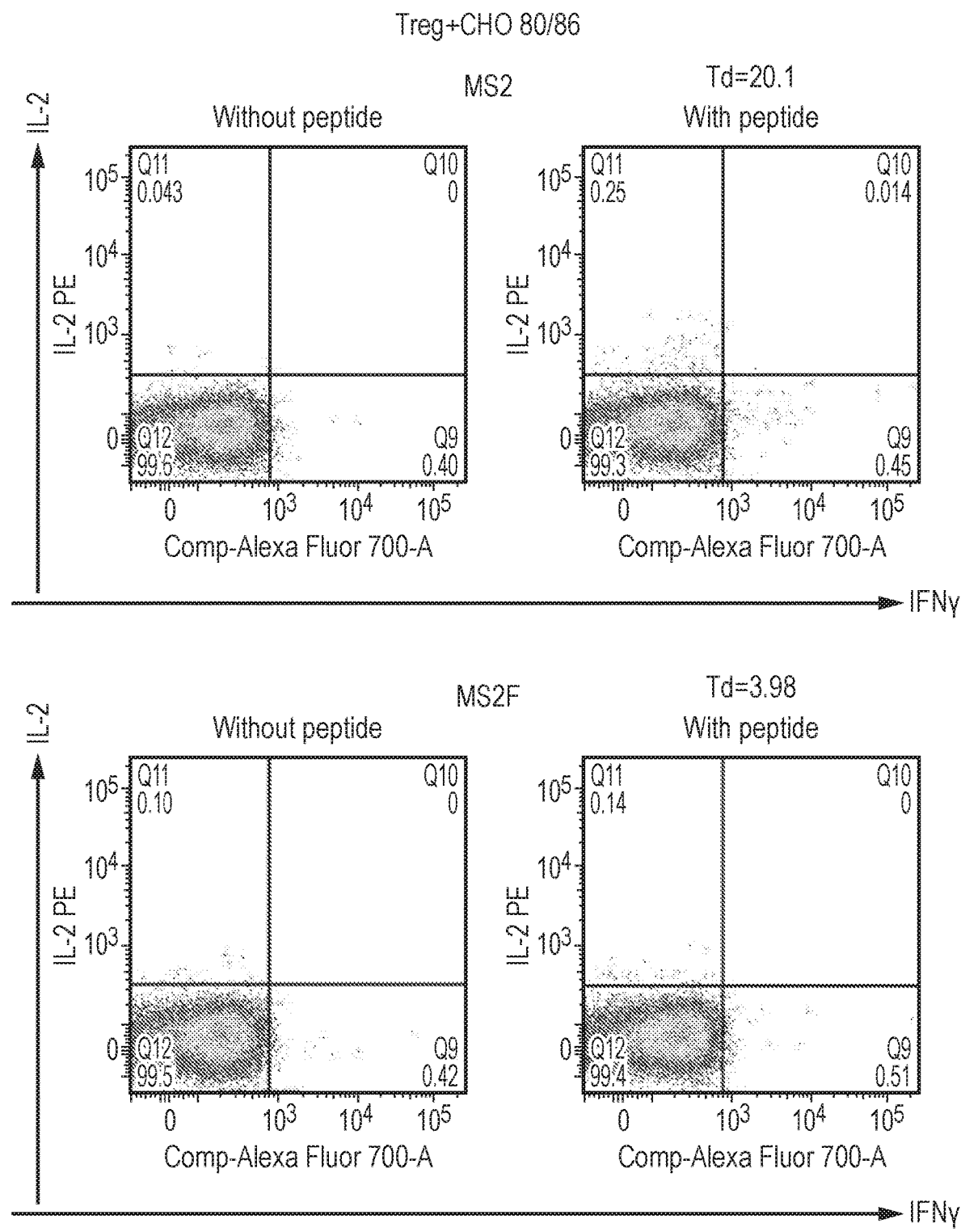
FIG. 8—Graphs showing restimulation of Treg cells with peptide. The method was described above for FIG. 7, using Tregs instead of effector T cells.

Treg cells were cultured with CHO cells as described above. FIG. 8 demonstrates FACS dot-plots showing peptide restimulation of Treg cells. The transduction efficiency of T cells is indicated by 'Td='.

Figure 9:
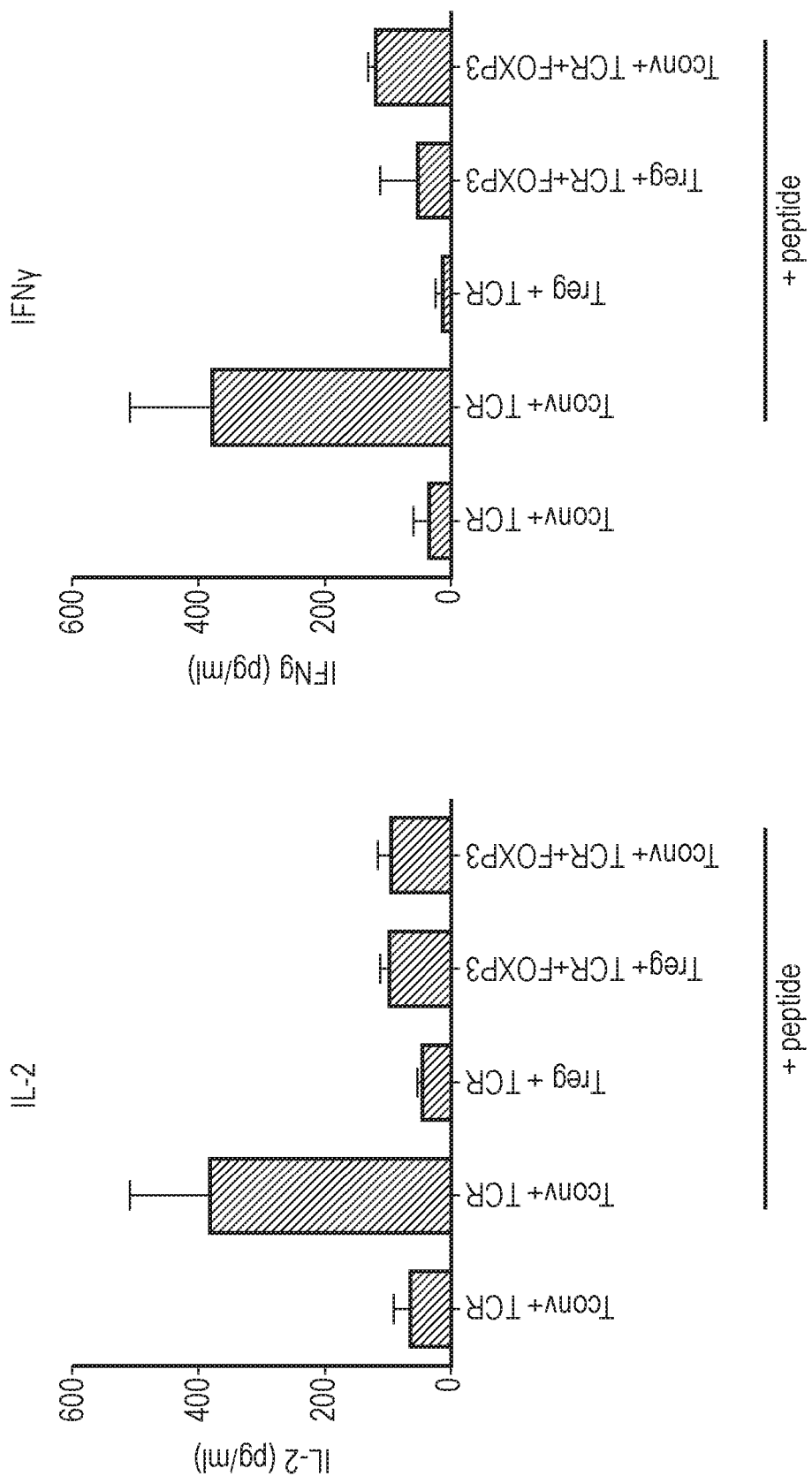
FIG. 9—Transduced T cells were cultured for 4 days with or without pepide-pulsed irradtiated APC. Supernatant was collected and assayed for IL-2 and IFNg by ELISA (n=2-4)

Example 5—TCR-Transduced and TCR-FOXP3 Transduced T Cells Response to Cognate Peptide TCR-transduced T cony, TCR-transduced Tregs, TCR-FOXP3 converted Tconv and TCR-FOXP3 converted Tconv (methods described above) were cultured for 4 days with or without pepide-pulsed irradiated APC. Supernatant was collected from the culture and assayed for IL-2 and IFNγ by ELISA (n=2-4). FIG. 9 shows that TCR-transduced Treg and TCR-FOXP3 converted Tconv response to cognate peptide.

Example 6—TCR-Transduced and TCR-FOXP3 Transduced

CHO cells were prepared as described above. T cony cells were transduced with TCR or with TCR+FOXP3. Transduced T cells were isolated by magnetic bead sorting. Transduced cells were stained with an anti-murine constant beta antibody conjugated to APC. Cells were thoroughly washed and stained with a second anti-APC antibody. Cells were washed and passed through a magnetic column and transduced cells were captured and eluted. Routinely >95% of purified cells were APC+.

Unstimulated cells cultured without CHO cells acted as a negative control. PMA (phorbol 12-myristate 13-acetate) stimulated cells acted as a positive control. White bars show cytokine production from cells expressing the MS2 TCR and black bars show cytokine production from T cells expressing MS2 TCR and FOXP3 (n=3). FIG. 10 shows that conventional T cells transduced with TCR and TCR+FOXP3 produce less IL-2 than conventional cells transduced with TCR alone.

Antigen-Specific Suppression of MS-2 TCR Transduced Tregs

Example 7—Proliferation of TCR-Transduced T Cells

CD80+CD86+DR4+ CHO cells were loaded with peptide and irradiated as described above before being resuspended at $0.1\times10^6$ cells/ml. Transduced responder T cells were stained with CFSE cell trace dye in warmed PBS at 37 degrees for 3 minutes before addition of equal volumes of warm FBS and a further 3 minute incubation.

Cells were washed in 5× volume of complete media before being counting and resuspended at $1\times10^6$ transduced cells/ml. The transduction efficiency of Tconv and Treg were determined by flow cytometry. Regulatory T cells are removed from culture, washed and resuspended at $1\times10^6$ transduced cells/ml in complete RPMI. Cells were plated 1 Treg:0.1 CHO cells:and varying ratios of Tconv. Proliferation was determined by analysing dilution of carboxyfluorescein succinimidyl ester (CFSE)-stained T cony.

The data in FIG. 11 show that TCR-transduced Tregs suppress proliferation in an antigen-specific manner. Supernatants were collected from the culture media and were assayed for IL-2 by ELISA. The data presented in FIG. 12 show that TCR-transduced Treg suppress IL-2 production in an antigen-specific manner.

Example 8—Engineered Tregs in an Adoptive Transfer Model of Experimental Autoimmune Encephalomyelitis Human conventional T cells which have been transduced with MS2-3C8 TCR are administered to immunodeficient NOD scid gamma mice (NSG) transgenic for HLADRB1*0401 by adoptive transfer.

Adoptive transfer of the human T cells may induce an experimental autoimmune encephalomyelitis (EAE) type disease in the mice. The mice are then treated with human Treg cells which have been transduced with MS2-3C8 TCR or control Tregs.

HLA-DRB1+0401-restricted MBP 111-129 (SEQ ID NO: 3)-specific humanised TCR transgenic mice have infiltrates of MS2-3C8 transgenic T cells and inflammatory legions located in the brainstem and the cranial nerve roots in addition to the spinal cord and spinal nerve roots (Quandt et al., J. Exp. Med. V. 200(2); 2004 incorporated herein by reference).

The suppression of proliferation of pathogenic T cells by TCR induced Tregs is measured in the mouse model e.g. by CFSE, IL-2 and/or IFNγ levels.

Example 9—Engineered Tregs in Classical Model of Experimental Autoimmune Encephalomyelitis Mice are immunised with Mog (myelin oligodendrocyte protein) to induce EAE, a widely accepted animal model of MS.

The mice are then treated with human Treg cells which have been transduced with MS2-3C8 TCR or control Tregs.

The suppression of proliferation of pathogenic T cells by TCR induced Tregs is measured in the mouse model e.g. by CFSE, IL-2 and/or IFNγ levels.

Example 10—TCR Transduced Regulatory T Cells can Engraft into Irradiated Hosts CD4+CD25+ Treg were isolated from lymph nodes and splenocytes of HLA-DRB*0401 transgenic mice by bead sort. Treg were transduced with TCR. 1 day after transduction TCR or TCR+FOXP3 transduced cells were injected into HLA-DRB*0401 transgenic hosts conditioned with 4 Gy irradiation (day 0). 7 weeks later flow cytometry was used to determine the engraftment of transduced Treg via staining for TCR (+7 weeks).

The results in FIG. 23 show persistence of Tregs and an antigen-specific suppressive effect 7 weeks post-administration.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. An isolated engineered human regulatory T cell (Treg) comprising a T cell receptor (TCR) which is capable of specifically binding to a peptide which comprises MBP 111-129 (SEQ ID NO: 3) when the peptide is presented by a HLA-DRB1*0401 molecule, wherein the TCR comprises an α chain and a β chain, wherein the α chain of the TCR comprises complementarity determining regions (CDRs) CDR1α, CDR2α, and CDR3α, having the following amino acid sequences:

```
                                       (SEQ ID NO: 7)
CDR1α - TISGTDY (SEQ ID NO: 8)
CDR2α - GLTSN (SEQ ID NO: 9)
CDR3α - TVYGGATNKLIFGTGTLLAVQPNIQNPD;
``` and
wherein the β chain of the TCR comprises CDRs CDR1β, CDR2β, and CDR3β, having the following amino acid sequences:

```
                                       (SEQ ID NO: 10)
CDR1β - DFQATT (SEQ ID NO: 11)
CDR2β - SNEGSKA (SEQ ID NO: 12)
CDR3β - SARGGSYNSPLHFGNGTRLTVTE;
``` and
wherein the engineered human Treg comprises an expression vector encoding the TCR and a human FOXP3 polypeptide comprising the amino acid sequence of SEQ ID NO: 17 or 25.

2. The isolated engineered human Treg according to claim 1, wherein:
(a) the α chain of the TCR comprises an α chain variable region comprising an amino acid sequence having at least 95% sequence identity to SEQ ID NO: 19; and
(b) the β chain of the TCR comprises a β chain variable region comprising an amino acid sequence having at least 95% sequence identity to SEQ ID NO: 21.

3. The isolated engineered human Treg according to claim 1, wherein the TCR comprises an α chain constant region and a β chain constant region, wherein each of the α chain constant region and the β chain constant region of the TCR comprises an additional cysteine residue, enabling the formation of an extra disulfide bond between the α chain and the β chain.

4. The isolated engineered human Treg according to claim 1, wherein:
(a) the TCR comprises an α chain comprising an amino acid sequence having at least 95% sequence identity to SEQ ID NO: 13; and
(b) the TCR comprises a β chain comprising an amino acid sequence having at least 95% sequence identity to SEQ ID NO: 14.

5. The isolated engineered human Treg according to claim 1, wherein the isolated engineered human Treg is produced by introducing into a CD4+CD25+ or CD4+CD25-T cell isolated from a human subject said expression vector.

6. A pharmaceutical composition comprising the isolated engineered human Treg according to claim 1.

7. A method for treating multiple sclerosis in a HLA-DRB1*0401 positive human subject, the method comprising administering to the HLA-DRB1*0401 positive human subject the isolated engineered human Treg according to claim 1.

8. An isolated vector which comprises (i) a nucleic acid sequence which encodes a TCR which is capable of specifically binding to a peptide which comprises MBP 111-129 (SEQ ID NO: 3) when the peptide is presented by a HLA-DRB1*0401 molecule, and (ii) a nucleic acid sequence which encodes a human FOXP3 polypeptide, wherein the TCR comprises an α chain and a β chain,
wherein the α chain of the TCR comprises complementarity determining regions (CDRs) CDR1α, CDR2α, and CDR3α, having the following amino acid sequences:

```
CDR1α - TISGTDY (SEQ ID NO: 7)

CDR2α - GLTSN (SEQ ID NO: 8)

CDR3α - TVYGGATNKLIFGTGTLLAVQPNIQNPD
(SEQ ID NO: 9);
``` and
wherein the β chain of the TCR comprises CDRs CDR1β, CDR2β, and CDR3β, having the following amino acid sequences:

```
CDR1β - DFQATT (SEQ ID NO: 10)

CDR2β - SNEGSKA (SEQ ID NO: 11)

CDR3β - SARGGSYNSPLHFGNGTRLTVTE (SEQ ID NO: 12);
``` and
wherein the human FOXP3 polypeptide comprises the amino acid sequence of SEQ ID NO: 17 or 25.

9. A kit comprising (i) a first nucleic acid sequence which encodes a TCR which is capable of specifically binding to a peptide which comprises MBP 111-129 (SEQ ID NO: 3) when the peptide is presented by a HLA-DRB1*0401 molecule, or a vector comprising the first nucleic acid sequence; and (ii) a second nucleic acid sequence which encodes a human FOXP3 polypeptide, or a vector comprising the second nucleic acid sequence, wherein the TCR comprises an α chain and a β chain,
wherein the α chain of the TCR comprises complementarity determining regions (CDRs) CDR1α, CDR2α, and CDR3α, having the following amino acid sequences:

```
CDR1α - TISGTDY (SEQ ID NO: 7)

CDR2α - GLTSN (SEQ ID NO: 8)

CDR3α - TVYGGATNKLIFGTGTLLAVQPNIQNPD
(SEQ ID NO: 9);
``` and
wherein the β chain of the TCR comprises CDRs CDR1β, CDR2β, and CDR3β, having the following amino acid sequences:

```
CDR1β - DFQATT (SEQ ID NO: 10)
CDR2β - SNEGSKA (SEQ ID NO: 11)
CDR3β - SARGGSYNSPLHFGNGTRLTVTE (SEQ ID NO: 12);
``` and
wherein the human FOXP3 polypeptide comprises the amino acid sequence of SEQ ID NO: 17 or 25.

10. A method for producing the isolated engineered human Treg according to claim 1, the method comprising introducing into a CD4+CD25+ or CD4+CD25-T cell in vitro or ex vivo said expression vector encoding the TCR and the human FOXP3 polypeptide.

11. The method according to claim 10 wherein the human T cell is $CD4^+CD25^+FOXP3^+$.

* * * * *

```
                      SEQUENCE LISTING

<160> NUMBER OF SEQ ID NOS: 27

<210> SEQ ID NO 1
<211> LENGTH: 304
<212> TYPE: PRT
<213> ORGANISM: Artificial Sequence
<220> FEATURE:
<223> OTHER INFORMATION: UniProtKB accession P02686-1

<400> SEQUENCE: 1

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140
```

```
Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
        210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
                260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro Met Ala Arg Arg
    290                 295                 300

<210> SEQ ID NO 2
<211> LENGTH: 41
<212> TYPE: PRT
<213> ORGANISM: Artificial Sequence
<220> FEATURE:
<223> OTHER INFORMATION: MBP 100-140

<400> SEQUENCE: 2

Pro Pro Ser Gln Gly Lys Gly Arg Gly Leu Ser Leu Ser Arg Phe Ser
1               5                   10                  15

Trp Gly Ala Glu Gly Gln Arg Pro Gly Phe Gly Tyr Gly Gly Arg Ala
            20                  25                  30

Ser Asp Tyr Lys Ser Ala His Lys Gly
        35                  40

<210> SEQ ID NO 3
<211> LENGTH: 19
<212> TYPE: PRT
<213> ORGANISM: Artificial Sequence
<220> FEATURE:
<223> OTHER INFORMATION: MBP 111-129

<400> SEQUENCE: 3

Leu Ser Arg Phe Ser Trp Gly Ala Glu Gly Gln Arg Pro Gly Phe Gly
1               5                   10                  15

Tyr Gly Gly

<210> SEQ ID NO 4
<211> LENGTH: 8
<212> TYPE: PRT
<213> ORGANISM: Artificial Sequence
<220> FEATURE:
<223> OTHER INFORMATION: MBP 116-123

<400> SEQUENCE: 4

Trp Gly Ala Glu Gly Gln Arg Pro
1               5

<210> SEQ ID NO 5
```

```
<211> LENGTH: 28
<212> TYPE: PRT
<213> ORGANISM: Artificial Sequence
<220> FEATURE:
<223> OTHER INFORMATION: CDR3alpha

<400> SEQUENCE: 5

Thr Val Tyr Gly Gly Ala Thr Asn Lys Leu Ile Phe Gly Thr Gly Thr
1               5                   10                  15
Leu Leu Ala Val Gln Pro Asn Ile Gln Asn Pro Asp
            20                  25

<210> SEQ ID NO 6
<211> LENGTH: 23
<212> TYPE: PRT
<213> ORGANISM: Artificial Sequence
<220> FEATURE:
<223> OTHER INFORMATION: CDR3beta

<400> SEQUENCE: 6

Ser Ala Arg Gly Gly Ser Tyr Asn Ser Pro Leu His Phe Gly Asn Gly
1               5                   10                  15
Thr Arg Leu Thr Val Thr Glu
            20

<210> SEQ ID NO 7
<211> LENGTH: 7
<212> TYPE: PRT
<213> ORGANISM: Artificial Sequence
<220> FEATURE:
<223> OTHER INFORMATION: CDR1alpha

<400> SEQUENCE: 7

Thr Ile Ser Gly Thr Asp Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: CDR2alpha

<400> SEQUENCE: 8

Gly Leu Thr Ser Asn
1               5

<210> SEQ ID NO 9
<211> LENGTH: 28
<212> TYPE: PRT
<213> ORGANISM: Artificial Sequence
<220> FEATURE:
<223> OTHER INFORMATION: CDR3alpha

<400> SEQUENCE: 9

Thr Val Tyr Gly Gly Ala Thr Asn Lys Leu Ile Phe Gly Thr Gly Thr
1               5                   10                  15
Leu Leu Ala Val Gln Pro Asn Ile Gln Asn Pro Asp
            20                  25

<210> SEQ ID NO 10
<211> LENGTH: 6
<212> TYPE: PRT
<213> ORGANISM: Artificial Sequence
<220> FEATURE:
<223> OTHER INFORMATION: CDR1beta
```

-continued

```
<400> SEQUENCE: 10

Asp Phe Gln Ala Thr Thr
1               5

<210> SEQ ID NO 11
<211> LENGTH: 7
<212> TYPE: PRT
<213> ORGANISM: Artificial Sequence
<220> FEATURE:
<223> OTHER INFORMATION: CDR2beta

<400> SEQUENCE: 11

Ser Asn Glu Gly Ser Lys Ala
1               5

<210> SEQ ID NO 12
<211> LENGTH: 23
<212> TYPE: PRT
<213> ORGANISM: Artificial Sequence
<220> FEATURE:
<223> OTHER INFORMATION: CDR3beta

<400> SEQUENCE: 12

Ser Ala Arg Gly Gly Ser Tyr Asn Ser Pro Leu His Phe Gly Asn Gly
1               5                   10                  15

Thr Arg Leu Thr Val Thr Glu
            20

<210> SEQ ID NO 13
<211> LENGTH: 250
<212> TYPE: PRT
<213> ORGANISM: Artificial Sequence
<220> FEATURE:
<223> OTHER INFORMATION: Human alpha V-region and murine constant-region

<400> SEQUENCE: 13

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Thr Val Tyr Gly Gly Ala Thr Asn
                85                  90                  95

Lys Leu Ile Phe Gly Thr Gly Thr Leu Leu Ala Val Gln Pro Asn Ile
            100                 105                 110

Gln Asn Pro Asp Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
    130                 135                 140

Pro Lys Thr Met Glu Ser Gly Thr Phe Ile Thr Asp Lys Cys Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
```

```
            180                 185                 190
Thr Tyr Pro Ser Ser Asp Val Pro Cys Asp Ala Thr Leu Thr Glu Lys
            195                 200                 205

Ser Phe Glu Thr Asp Met Asn Leu Asn Phe Gln Asn Leu Ser Val Met
        210                 215                 220

Gly Leu Arg Ile Leu Leu Lys Val Ala Gly Phe Asn Leu Leu Met
225                 230                 235                 240

Thr Leu Arg Leu Trp Ser Ser Gly Ser Gly
            245                 250

<210> SEQ ID NO 14
<211> LENGTH: 289
<212> TYPE: PRT
<213> ORGANISM: Artificial sequence
<220> FEATURE:
<223> OTHER INFORMATION: Human beta V-region and murine constant-region

<400> SEQUENCE: 14

Gly Ala Val Val Ser Gln His Pro Ser Trp Val Ile Ala Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Gly Gly Ser Tyr Asn Ser Pro Leu His Phe Gly Asn Gly Thr Arg
            100                 105                 110

Leu Thr Val Thr Glu Asp Leu Arg Asn Val Thr Pro Pro Lys Val Ser
        115                 120                 125

Leu Phe Glu Pro Ser Lys Ala Glu Ile Ala Asn Lys Gln Lys Ala Thr
130                 135                 140

Leu Val Cys Leu Ala Arg Gly Phe Phe Pro Asp His Val Glu Leu Ser
145                 150                 155                 160

Trp Trp Val Asn Gly Lys Glu Val His Ser Gly Val Cys Thr Asp Pro
                165                 170                 175

Gln Ala Tyr Lys Glu Ser Asn Tyr Ser Tyr Cys Leu Ser Ser Arg Leu
            180                 185                 190

Arg Val Ser Ala Thr Phe Trp His Asn Pro Arg Asn His Phe Arg Cys
        195                 200                 205

Gln Val Gln Phe His Gly Leu Ser Glu Glu Asp Lys Trp Pro Glu Gly
    210                 215                 220

Ser Pro Lys Pro Val Thr Gln Asn Ile Ser Ala Glu Ala Trp Gly Arg
225                 230                 235                 240

Ala Asp Cys Gly Ile Thr Ser Ala Ser Tyr His Gln Gly Val Leu Ser
                245                 250                 255

Ala Thr Ile Leu Tyr Glu Ile Leu Leu Gly Lys Ala Thr Leu Tyr Ala
            260                 265                 270

Val Leu Val Ser Gly Leu Val Leu Met Ala Met Val Lys Lys Lys Asn
        275                 280                 285

Ser
```

<210> SEQ ID NO 15
<211> LENGTH: 17
<212> TYPE: PRT
<213> ORGANISM: Artificial Sequence
<220> FEATURE:
<223> OTHER INFORMATION: Leader sequence

<400> SEQUENCE: 15

Met Lys Leu Val Thr Ser Ile Thr Val Leu Leu Ser Leu Gly Ile Met
1               5                   10                  15

Gly

<210> SEQ ID NO 16
<211> LENGTH: 25
<212> TYPE: PRT
<213> ORGANISM: Artificial Sequence
<220> FEATURE:
<223> OTHER INFORMATION: Leader sequence

<400> SEQUENCE: 16

Met Leu Leu Leu Leu Leu Leu Leu Gly Pro Gly Ile Ser Leu Leu Leu
1               5                   10                  15

Pro Gly Ser Leu Ala Gly Ser Gly Leu
            20                  25

<210> SEQ ID NO 17
<211> LENGTH: 431
<212> TYPE: PRT
<213> ORGANISM: Artificial Sequence
<220> FEATURE:
<223> OTHER INFORMATION: FOXP3 polypeptide - UniProtKB accession: Q9BZS1

<400> SEQUENCE: 17

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
                100                 105                 110

Ala Arg Thr Pro Val Leu Gln Val His Pro Leu Glu Ser Pro Ala Met
            115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
                180                 185                 190

Leu Leu Ala Asn Gly Val Cys Lys Trp Pro Gly Cys Glu Lys Val Phe

```
                195                 200                 205
Glu Glu Pro Glu Asp Phe Leu Lys His Cys Gln Ala Asp His Leu Leu
    210                 215                 220
Asp Glu Lys Gly Arg Ala Gln Cys Leu Leu Gln Arg Glu Met Val Gln
225                 230                 235                 240
Ser Leu Glu Gln Gln Leu Val Leu Glu Lys Glu Lys Leu Ser Ala Met
                245                 250                 255
Gln Ala His Leu Ala Gly Lys Met Ala Leu Thr Lys Ala Ser Ser Val
            260                 265                 270
Ala Ser Ser Asp Lys Gly Ser Cys Cys Ile Val Ala Ala Gly Ser Gln
        275                 280                 285
Gly Pro Val Val Pro Ala Trp Ser Gly Pro Arg Glu Ala Pro Asp Ser
    290                 295                 300
Leu Phe Ala Val Arg Arg His Leu Trp Gly Ser His Gly Asn Ser Thr
305                 310                 315                 320
Phe Pro Glu Phe Leu His Asn Met Asp Tyr Phe Lys Phe His Asn Met
                325                 330                 335
Arg Pro Pro Phe Thr Tyr Ala Thr Leu Ile Arg Trp Ala Ile Leu Glu
            340                 345                 350
Ala Pro Glu Lys Gln Arg Thr Leu Asn Glu Ile Tyr His Trp Phe Thr
        355                 360                 365
Arg Met Phe Ala Phe Phe Arg Asn His Pro Ala Thr Trp Lys Asn Ala
    370                 375                 380
Ile Arg His Asn Leu Ser Leu His Lys Cys Phe Val Arg Val Glu Ser
385                 390                 395                 400
Glu Lys Gly Ala Val Trp Thr Val Asp Glu Leu Glu Phe Arg Lys Lys
                405                 410                 415
Arg Ser Gln Arg Pro Ser Arg Cys Ser Asn Pro Thr Pro Gly Pro
            420                 425                 430

<210> SEQ ID NO 18
<211> LENGTH: 408
<212> TYPE: DNA
<213> ORGANISM: Artificial Sequence
<220> FEATURE:
<223> OTHER INFORMATION: Alpha Chain: V-region, MS2.3C8-alpha-
      variable(Va26-2) nucleotide sequence

<400> SEQUENCE: 18
cccggaccga tgaagctcgt gaccagcatc accgtgctgc tgagcctggg cattatgggc    60
gacgccaaga ccacccagcc caacagcatg gaaagcaacg aagaggaacc cgtgcatctg   120
ccctgcaacc acagcaccat cagcggcacc gactacatcc actggtacag acagctgccc   180
agccagggcc ccgagtatgt gatccacggc ctgaccagca cgtgaacaa ccggatggcc   240 tccctggcca ttgccgagga cagaaagagc agcaccctga tcctgcaccg ggccaccctg   300
agagatgccg ccgtgtacta ctgcaccgtg tacggcggag ccaccaacaa gctgatcttc   360
ggcaccggca cactgctggc cgtgcagccc aatatccaga accccgac              408

<210> SEQ ID NO 19
<211> LENGTH: 116
<212> TYPE: PRT
<213> ORGANISM: Artificial Sequence
<220> FEATURE:
<223> OTHER INFORMATION: Alpha Chain: V-region, MS2.3C8-alpha-
      variable(Va26-2) amino acid sequence

<400> SEQUENCE: 19
```

Asp Ala Lys Thr Thr Gln Pro Asn Ser Met Glu Ser Asn Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Met Ala Ser Leu Ala Ile
        50                  55                  60

Ala Glu Asp Arg Lys Ser Ser Thr Leu Ile Leu His Arg Ala Thr Leu
65              70                  75                  80

Arg Asp Ala Ala Val Tyr Tyr Cys Thr Val Tyr Gly Gly Ala Thr Asn
                85                  90                  95

Lys Leu Ile Phe Gly Thr Gly Thr Leu Leu Ala Val Gln Pro Asn Ile
                100                 105                 110

Gln Asn Pro Asp
        115

<210> SEQ ID NO 20
<211> LENGTH: 423
<212> TYPE: DNA
<213> ORGANISM: Artificial Sequence
<220> FEATURE:
<223> OTHER INFORMATION: MS2.3C8 Beta Chain: human V-region nucleotide
      sequence

<400> SEQUENCE: 20
atgcttctcc ttctgctgct gctgggaccc ggcatctcac tgctgctgcc tggatctctg      60
gccggctctg gactgggagc tgtggtgtct cagcacccct cttgggtcat cgccaagagc     120
ggcaccagcg tgaagatcga gtgcagaagc ctggacttcc aggccaccac catgttttgg     180
tacaggcagt tccccaagca gagcctgatg ctgatggcca cctccaacga gggcagcaag     240
gccacatatg agcagggcgt ggaaaaggac aagttcctga tcaaccacgc cagcctgacc     300
ctgtccaccc tgacagtgac aagcgcccac cccgaggact ccagcttcta catctgtagc     360
gccagaggcg gcagctacaa cagccctctg cactttggca acggcacccg gctgaccgtg     420
acc                                                                   423

<210> SEQ ID NO 21
<211> LENGTH: 111
<212> TYPE: PRT
<213> ORGANISM: Artificial Sequence
<220> FEATURE:
<223> OTHER INFORMATION: MS2.3C8 Beta Chain: human V-region amino acid
      sequence

<400> SEQUENCE: 21

Gly Ala Val Val Ser Gln His Pro Ser Trp Val Ile Ala Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Ser Cys Ser Trp Pro
            35                  40                  45

Pro Pro Thr Arg Ala Pro Arg Pro Thr Ser Arg Ala Ser Arg Arg
        50                  55                  60

Thr Ser Ser Ser Thr Thr Pro Pro Ser Pro Pro Ser Pro Pro Ser Pro
65              70                  75                  80

Ser Pro Pro Pro Thr Pro Arg Thr Pro Pro Ser Thr Ser Ala Pro Pro

```
                    85                  90                  95
Ala Ala Ala Pro Thr Thr Pro Pro Ser Thr Ser Ala Thr Ala Pro
            100                 105                 110

<210> SEQ ID NO 22
<211> LENGTH: 76
<212> TYPE: PRT
<213> ORGANISM: Artificial Sequence
<220> FEATURE:
<223> OTHER INFORMATION: MS2.3C8-alpha-variable amino acid sequence
      excluding CDR sequences

<400> SEQUENCE: 22

Asp Ala Lys Thr Thr Gln Pro Asn Ser Met Glu Ser Asn Glu Glu
1               5                   10                  15

Pro Val His Leu Pro Cys Asn His Ser Ile His Trp Tyr Arg Gln Leu
            20                  25                  30

Pro Ser Gln Gly Pro Glu Tyr Val Ile His Val Asn Asn Arg Met Ala
        35                  40                  45

Ser Leu Ala Ile Ala Glu Asp Arg Lys Ser Ser Thr Leu Ile Leu His
    50                  55                  60

Arg Ala Thr Leu Arg Asp Ala Val Tyr Tyr Cys
65                  70                  75

<210> SEQ ID NO 23
<211> LENGTH: 81
<212> TYPE: PRT
<213> ORGANISM: Artificial Sequence
<220> FEATURE:
<223> OTHER INFORMATION: MS2.3C8-beta-variable amino acid sequence
      excluding CDR sequences

<400> SEQUENCE: 23

Gly Ala Val Val Ser Gln His Pro Ser Trp Val Ile Ala Lys Ser Gly
1               5                   10                  15

Thr Ser Val Lys Ile Glu Cys Arg Ser Leu Met Phe Trp Tyr Arg Gln
            20                  25                  30

Phe Pro Lys Gln Ser Leu Met Leu Met Ala Thr Thr Tyr Glu Gln Gly
        35                  40                  45

Val Glu Lys Asp Lys Phe Leu Ile Asn His Ala Ser Leu Thr Leu Ser
    50                  55                  60

Thr Leu Thr Val Thr Ser Ala His Pro Glu Asp Ser Ser Phe Tyr Ile
65                  70                  75                  80

Cys

<210> SEQ ID NO 24
<211> LENGTH: 1352
<212> TYPE: DNA
<213> ORGANISM: Artificial Sequence
<220> FEATURE:
<223> OTHER INFORMATION: Nucleic acid sequence encoding FOXP3

<400> SEQUENCE: 24
gaattcgtcg acatgcccaa ccccagaccc ggcaagcctt ctgccccttc tctggccctg      60
ggaccatctc ctggcgcctc cccatcttgg agagccgccc taaagccag cgatctgctg     120 ggagctagag gcctggcgg cacattccag gcagagatc tgagaggcgg agcccacgcc      180
tctagcagca gctgaatcc catgccccct agccagctgc agctgcctac actgcctctc      240
gtgatggtgg cccctagcgg agctagactg ggccctctgc tcatctgca ggctctgctg      300
```

```
caggaccggc cccactttat gcaccagctg agcaccgtgg acgcccacgc cagaacacct    360
gtgctgcagg tgcaccccct ggaaagccct gccatgatca gcctgacccc tccaaccaca    420
gccaccggcg tgttcagcct gaaggccaga cctggactgc cccctggcat caatgtggcc    480
agcctggaat gggtgtcccg cgaacctgcc ctgctgtgca ccttccccaa tcctagcgcc    540
cccagaaagg acagcacact gtctgccgtg ccccagagca gctatcccct gctggctaac    600
ggcgtgtgca gtggcctggc tgcgagaag gtgttcgagg aacccgagga cttcctgaag    660
cactgccagg ccgaccatct gctggacgag aaaggcagag cccagtgcct gctgcagcgc    720
gagatggtgc agtccctgga acagcagctg gtgctggaaa agaaaagct gagcgccatg    780 caggcccacc tggccggaaa gatggccctg acaaaagcca gcagcgtggc cagctccgac    840
aagggcagct gttgtatcgt ggccgctggc agccagggac ctgtggtgcc tgcttggagc    900
ggacctagag aggcccccga tagcctgttt gccgtgcgga cacctgtg gggcagccac    960 ggcaactcta ccttccccga gttcctgcac aacatggact acttcaagtt ccacaacatg   1020
aggcccccct tcacctacgc cacctgatc agatgggcca ttctggaagc ccccgagaag   1080
cagcggaccc tgaacgagat ctaccactgg tttacccgga tgttcgcctt cttccggaac   1140 cacccccgcca cctggaagaa cgccatccgg cacaatctga gcctgcacaa gtgcttcgtg   1200
cgggtggaaa gcgagaaggg cgccgtgtgg acagtggacg agctggaatt tcggaagaag   1260
cggtcccaga ggcccagccg gtgtagcaat cctacacctg ccctgagggg cagaggaagt   1320
ctgctaacat gcggtgacgt cgaggagaat cc                                 1352
```

<210> SEQ ID NO 25
<211> LENGTH: 441
<212> TYPE: PRT
<213> ORGANISM: Artificial Sequence
<220> FEATURE:
<223> OTHER INFORMATION: Amino acid sequence of FOXP3

<400> SEQUENCE: 25

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175
```

```
Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Val Glu Glu Leu Ser Ala Met Gln Ala His Leu Ala
            245                 250                 255

Gly Lys Met Ala Leu Thr Lys Ala Ser Ser Val Ala Ser Ser Asp Lys
        260                 265                 270

Gly Ser Cys Cys Ile Val Ala Ala Gly Ser Gln Gly Pro Val Val Pro
    275                 280                 285

Ala Trp Ser Gly Pro Arg Glu Ala Pro Asp Ser Leu Phe Ala Val Arg
290                 295                 300

Arg His Leu Trp Gly Ser His Gly Asn Ser Thr Phe Pro Glu Phe Leu
305                 310                 315                 320

His Asn Met Asp Tyr Phe Lys Phe His Asn Met Arg Pro Pro Phe Thr
            325                 330                 335

Tyr Ala Thr Leu Ile Arg Trp Ala Ile Leu Glu Ala Pro Glu Lys Gln
        340                 345                 350

Arg Thr Leu Asn Glu Ile Tyr His Trp Phe Thr Arg Met Phe Ala Phe
    355                 360                 365

Phe Arg Asn His Pro Ala Thr Trp Lys Asn Ala Ile Arg His Asn Leu
370                 375                 380

Ser Leu His Lys Cys Phe Val Arg Val Glu Ser Glu Lys Gly Ala Val
385                 390                 395                 400

Trp Thr Val Asp Glu Leu Glu Phe Arg Lys Lys Arg Ser Gln Arg Pro
            405                 410                 415

Ser Arg Cys Ser Asn Pro Thr Pro Gly Pro Gly Arg Gly Ser Leu
        420                 425                 430

Leu Thr Cys Gly Asp Val Glu Glu Asn
    435                 440

<210> SEQ ID NO 26
<211> LENGTH: 171
<212> TYPE: PRT
<213> ORGANISM: Artificial Sequence
<220> FEATURE:
<223> OTHER INFORMATION: UniProtKB accession P02686-5

<400> SEQUENCE: 26

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
            85                  90                  95
```

```
Pro Arg Thr Pro Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 27
<211> LENGTH: 1296
<212> TYPE: DNA
<213> ORGANISM: Artificial Sequence
<220> FEATURE:
<223> OTHER INFORMATION: FOXP3 polynucleotide sequence

<400> SEQUENCE: 27
atgcccaacc ccaggcctgg caagccctcg gcccttcct tggcccttgg cccatcccca      60
ggagcctcgc ccagctggag ggctgcaccc aaagcctcag acctgctggg ggcccggggc    120 ccaggggaa ccttccaggg ccgagatctt cgaggcgggg cccatgcctc ctcttcttcc     180 ttgaaccca tgccaccatc gcagctgcag ctgcccacac tgcccctagt catggtggca     240
ccctccgggg cacggctggg ccccttgccc cacttacagg cactcctcca ggacaggcca    300
catttcatgc accagctctc aacggtggat gcccacgccc ggacccctgt gctgcaggtg    360
caccccctgg agagcccagc catgatcagc ctcacaccac ccaccaccgc cactgggtc     420 ttctccctca aggcccggcc tggcctccca cctgggatca acgtggccag cctggaatgg    480
gtgtccaggg agccggcact gctctgcacc ttcccaaatc ccagtgcacc caggaaggac    540 agcaccctt cggctgtgcc ccagagctcc tacccactgc tggcaaatgg tgtctgcaag    600
tggcccggat gtgagaaggt cttcgaagag ccagaggact cctcaagca ctgccaggcg    660 gaccatcttc tggatgagaa gggcagggca caatgtctcc tccagagaga gatggtacag    720
tctctggagc agcagctggt gctggagaag gagaagctga gtgccatgca ggcccacctg    780
gctgggaaaa tggcactgac caaggcttca tctgtggcat catccgacaa gggctcctgc    840
tgcatcgtag ctgctggcag ccaaggccct gtcgtcccag cctggtctgg ccccgggag    900 gcccctgaca gctgtttgc tgtccggagg cacctgtggg gtagccatgg aaacagcaca    960
ttcccagagt cctccacaa catggactac ttcaagttcc acaacatgcg acccccttc    1020 acctacgcca cgctcatccg ctgggccatc ctggaggctc cagagaagca gcggacactc   1080
aatgagatct accactggtt cacacgcatg tttgccttct cagaaaccca tcctgccacc   1140
tggaagaacg ccatccgcca aacctgagt ctgcacaagt gctttgtgcg ggtggagagc   1200 gagaagggg ctgtgtggac cgtggatgag ctggagttcc gcaagaaacg gagccagagg   1260
cccagcaggt gttccaaccc tacacctggc ccctga                            1296
```